(12) United States Patent
Ali et al.

(10) Patent No.: US 11,867,648 B2
(45) Date of Patent: Jan. 9, 2024

(54) THERMAL FLUID SENSOR WITH ENCAPSULATED FLUID REGION

(71) Applicant: Flusso Limited, Cambridgeshire (GB)

(72) Inventors: Syed Zeeshan Ali, Cambridgeshire (GB); Cerdin Ching Ching Lee, Cambridgeshire (GB); Ethan Gardner, Warwickshire (GB); Jonathan Owen Hardie, Cambridgeshire (GB); Jonathan Sean Callan, Cambridgeshire (GB); Florin Udrea, Cambridgeshire (GB)

(73) Assignee: Flusso Limited, Cambridge (GB)

( * ) Notice: Subject to any disclaimer, the term of this patent is extended or adjusted under 35 U.S.C. 154(b) by 0 days.

(21) Appl. No.: 17/354,327

(22) Filed: Jun. 22, 2021

(65) Prior Publication Data
US 2022/0404300 A1    Dec. 22, 2022

(51) Int. Cl.
*G01N 25/18*    (2006.01)
*G01N 25/00*    (2006.01)
(Continued)

(52) U.S. Cl.
CPC ............ *G01N 25/18* (2013.01); *G01N 25/00* (2013.01); *G01N 25/48* (2013.01);
(Continued)

(58) Field of Classification Search
CPC .... G01N 25/18; G01N 33/0027; G01N 30/66; G01F 1/68
See application file for complete search history.

(56) References Cited

U.S. PATENT DOCUMENTS 5,804,720 A * 9/1998 Morimasa ............. G01F 1/6845
73/202.5
6,375,279 B1    4/2002 Cassidy
(Continued)

OTHER PUBLICATIONS

G. De Graaf et al., "Surface-micromachined thermal conductivity detectors for gas sensing." 2012 IEEE International Instrumentation and Measurement Technology Conference Proceedings, pp. 1861-1864.
(Continued)

*Primary Examiner* — Eric S. McCall
*Assistant Examiner* — Timothy P Graves
(74) *Attorney, Agent, or Firm* — Kilpatrick Townsend & Stockton LLP

(57) ABSTRACT

A fluid sensor for sensing a concentration or composition of a fluid, the sensor comprising: a semiconductor substrate comprising a first etched portion and a second etched portion; a dielectric region located on the semiconductor substrate, wherein the dielectric region comprises a first dielectric membrane located over the first etched portion of the semiconductor substrate, and a second dielectric membrane located over the second etched portion of the semiconductor substrate; two temperature sensing elements on or within the first dielectric membrane and two temperature sensing elements on or within the second dielectric membrane; an output circuit configured to measure a differential signal between the two temperature sensing elements of the first dielectric membrane and the two temperature sensing elements of the second dielectric membrane; wherein the first dielectric membrane is exposed to the fluid and the second dielectric membrane is isolated from the fluid.

21 Claims, 17 Drawing Sheets

(51) Int. Cl.
    *G01N 25/48*     (2006.01)
    *G01N 33/00*     (2006.01)

(52) U.S. Cl.
    CPC ..... *G01N 25/4873* (2013.01); *G01N 25/4893* (2013.01); *G01N 33/0004* (2013.01); *G01N 33/0027* (2013.01)

(56) References Cited

U.S. PATENT DOCUMENTS

| | | |
|---|---|---|
| 8,667,839 B2 | 3/2014 | Kimura |
| 8,689,608 B2 | 4/2014 | Nakano |
| 10,408,802 B2 | 9/2019 | Kumar |
| 10,598,621 B2 | 3/2020 | Liu |
| 2016/0025660 A1* | 1/2016 | Hepp ..................... G01N 25/00 73/25.05 |
| 2018/0292338 A1* | 10/2018 | Liu ........................ G01N 27/04 |

OTHER PUBLICATIONS

Mahdavifar et al. "Simulation and Fabrication of an Ultra-Low Power miniature Microbridge Thermal Conductivity Gas Sensor," 2014 Journal of the Electrochemical Society, 161 B55.

Kommandur et al., "A microbridge heater for low power gas sensing based on the 3-omega technique," Sensors and Actuators A 233 (2015) 231-238.

\* cited by examiner

THERMAL FLUID SENSOR WITH ENCAPSULATED FLUID REGION

TECHNICAL FIELD

The present disclosure relates to a micro-machined sensor, particularly but not exclusively, the disclosure relates to a fluid sensor for sensing concentration of a fluid or concentration of components of a fluid based on thermal conductivity of the fluid.

BACKGROUND

There is an increasing demand for gas sensors to monitor pollutants in our environment. Gas sensors can be based on many different principles and technologies. One such principle is using thermal conductivity to determine the composition of gases.

For example, in G. De Graaf and R. F. Wolffenbuttel, "Surface-micromachined thermal conductivity detectors for gas sensing." 2012 IEEE International Instrumentation and Measurement Technology Conference Proceedings, pp. 1861-1864, a thermal conductivity gas sensor based on silicon technology is described.

Mahdavifar et. al. in "Simulation and Fabrication of an Ultra-Low Power miniature Microbridge Thermal Conductivity Gas Sensor," Journal of the Electrochemical Society, 161 B55, describe a device comprising a suspended thin polysilicon resistor that acts as a heater and a temperature sensor as part of a thermal conductivity sensor. The change in resistance of the polysilicon with temperature allows its use as a temperature sensor.

U.S. Ser. No. 10/598,621, U.S. Pat. Nos. 8,667,839B2, and 6,375,279B1, 8,689,608 and U.S. Ser. No. 10/408,802B2 describe further sensors. Kommandur et. al., "A microbridge heater for low power gas sensing based on the 3-omega technique," Sensors and Actuators A 233 (2015) 231-238, also describes a thermal conductivity sensor.

SUMMARY

Presently available sensors have, among others, the following disadvantages:
  high power dissipation, low sensitivity and slow dynamic response of the sensor;
  mechanical fragility and vibration sensitivity;
  reduced mechanical robustness of sensor supporting structures;
  complex fabrication processes;
  manufacturing processes that are not fully CMOS compatible; and
  manufacturing processes that are expensive.

The devices of the present disclosure are advantageous over the state-of-the-art devices for the following reasons:
  the sensor is able to determine composition of a fluid and concentration of different components within the fluid, in a zero flow environment;
  thermal isolation of the heated element which reduces power dissipation, increases sensitivity and provides a fast, dynamic response of the sensor;
  reduced mechanical fragility and vibration sensitivity of the membrane structure compared to a beam structure;
  a suitable dielectric material used for the dielectric membrane improves mechanical robustness of the membrane;
  a suitable dielectric material used for the dielectric membrane reduces power dissipation, increases sensitivity and provides a fast, dynamic response of the sensor;
  discontinuities within the membrane mitigate power dissipation, sensitivity and dynamic response issues; and
  the devices are fully CMOS compatible and therefore can be manufactured using fully CMOS compatible processes.

The presently disclosed fluid sensor is able to measure the composition of the fluid based on the different thermal conductivity of each of the components of the fluid.

Aspects and preferred features are set out in the accompanying claims.

According to an aspect of the present disclosure, there is provided a fluid sensor for sensing a concentration or composition of a fluid, the sensor comprising a semiconductor substrate comprising a first etched portion and a second etched portion; a dielectric region located on the semiconductor substrate, wherein the dielectric region comprises a first dielectric membrane located over the first etched portion of the semiconductor substrate, and a second dielectric membrane located over the second etched portion of the semiconductor substrate; two temperature sensing elements on or within the first dielectric membrane and two temperature sensing elements on or within the second dielectric membrane; an output circuit configured to measure a differential signal between the two temperature sensing elements of the first dielectric membrane and the two temperature sensing elements of the second dielectric membrane; wherein the first dielectric membrane is exposed to the fluid and the second dielectric membrane is isolated from the fluid.

In some implementations, one or both of the temperature sensing elements within the first and second dielectric membranes are configured to operate as heating elements In some implementations, the first and second dielectric membrane comprise an additional heating element.

In other words, one of the temperature sensing elements in each of the dielectric membrane may also be a heating element. Alternately each dielectric membrane may have a separate heating element.

In some implementations, the output circuit comprises a wheatstone bridge, wherein the two temperature sensing elements from the first dielectric membrane or from the second dielectric membrane operate as respective first and second legs of the wheatstone bridge.

In some implementations, the sensor comprises an ambient temperature sensor on the semiconductor substrate.

In some implementations, the ambient temperature sensor operates as a respective third or fourth leg of the wheatstone bridge.

In some implementations, the two temperature sensing elements from the other of the first or second dielectric membrane operate as respective third and fourth legs of the wheatstone bridge. As will be described below, filling all four legs of a wheatstone bridge with said temperature sensors allows for a greatly improved device sensitivity.

In some implementations, the first and second dielectric membranes have the same size and shape, and the temperature sensing elements from the first and second dielectric membranes have the same size and shape.

In some implementations, the temperature sensing elements comprise one or more of: resistors, diodes, transistors, thermopiles, or a combination thereof.

In some implementations, the heating elements comprise resistors or transistors.

In some implementations, the sensor comprises an exposed region exposed to the fluid, and a sealed region sealed (for example, completely sealed) and isolated from the fluid.

In some implementations, the semiconductor substrate comprises separate first and second semiconductor substrate sections, the first semiconductor substrate part comprising the first dielectric membrane on the first etched portion, and the second semiconductor substrate section comprising the second dielectric membrane on the second etched portion, whereby the first semiconductor substrate section is in the exposed region and the second semiconductor substrate section is in the sealed region.

In some implementations, the semiconductor substrate comprises integral first and second semiconductor substrate sections, the first semiconductor substrate section being in the exposed region and the second semiconductor substrate section being in the sealed region, whereby the first dielectric membrane is in the exposed region and the second dielectric membrane is in the sealed region.

In some implementations, the sealed region is sealed containing one or more of: air, dry air, synthetic air, an inert gas such as nitrogen or argon, a vacuum, or a partial vacuum. Alternatively the sealed region can contain a gas with a known composition. For example if the CO2 concentration in air is to be detected by the fluid sensor of the present disclosure, it would be possible to seal the region with a known concentration of $CO_2$. This concentration could be any known level from its typical concentration in air 400 pmm to any level to 100% $CO_2$.

In some implementations, the sensor comprises an ASIC.

In some implementations, the ASIC operates as a base of the sensor and comprises one or more through-silicon vias for making electrical connections.

In some implementations, the sensor is arranged in a flip-chip configuration.

In some implementations, the output circuit comprises one or more of: a constant current source, a wheatstone bridge, a differential amplifier, an instrumentation amplifier, an analogue to digital convertor and a micro-controller.

In some implementations, the wheatstone bridge is arranged to be balanced by a change of a bias of one or more of a heating element or temperature sensing element operating as a heating element on the first or second dielectric membranes.

These and other implementations are explained in more detail as follows. The sensor may be provided with first and second identical dielectric membranes, identical heating elements on the first and second dielectric membranes, and two resistive temperature sensing elements each on the first and second dielectric membranes that are identical in terms of size, shape and materials. For most electrically conductive materials the electrical resistance changes with temperature, so the change in resistance of the resistive temperature sensing elements corresponds to the change in temperature of the membrane. Preferably the temperature sensing elements will be made with a material having a high Temperature Coefficient of Resistance (TCR) so as to have a high sensitivity.

In operation, the heating elements of the first and second dielectric membrane are biased to heat up the membranes to a high temperature. The bias to the heater can be a constant current, constant voltage or constant power bias. Because the first dielectric membrane is exposed to the surrounding fluid, change in thermal conductivity of the surrounding fluid (due to change in fluid composition) will cause a change in the heat loss from the membrane, and hence a temperature change on the first dielectric membrane. Because the second dielectric membrane is isolated from the surrounding fluid, it is not affected by the change in fluid composition. Hence, the difference in temperature between the first and second membrane will be affected by change in fluid composition, and will be detected by the readout circuit comprising the four temperature sensing elements.

Advantageously, the resistive temperature sensing elements maybe connected as part of a readout or output circuit, with the four temperature sensing elements operating as legs of a wheatstone bridge. The two temperature sensing elements from the first dielectric membrane are envisaged to be on opposite sides to each other within the wheatstone bridge, and similarly the two temperature sensing elements from the second dielectric membrane will be on opposite sides to each other within the wheatstone bridge. When the temperatures on both the membranes are the same, the wheatstone bridge will output zero volts. But when the temperature on one of the membranes changes, then the wheatstone bridge will be unbalanced and will give an output voltage. Further circuitry such as an instrumentation amplifier and analogue to digital convertor may also be present.

Compared to providing only one temperature sensing element on each membrane, providing two temperature sensing elements on each dielectric membrane, allows all four branches or legs of the wheatstone bridge to be filled with said temperature sensing elements, thereby doubling the sensitivity of the device compared to a scenario where only two legs of a single wheatstone bridge are filled with temperature sensing elements (the other legs being filled by, for example, known value resistors).

Another way to operate the device is using a feedback loop. The four temperature sensing elements are part of a wheatstone bridge whose output is normally zero. In presence of the target gas the heating element on the first membrane will have lower or higher thermal losses, and hence the temperature of the first membrane will change causing the wheatstone bridge to be unbalanced and give an output value based on the change in temperature. A feedback control circuit can then be used to change the bias on the heating element on the first membrane until the bridge is balanced again and gives a zero output. The bias on the heating element is then used as the value to determine the composition of the surrounding fluid.

While ideally the heating elements should be identical, and the temperature sensing elements should be identical, in practice there may be small differences due to fabrication tolerances. This can be accounted for by calibration of the device in known conditions before use. Based on the calibration, the device may then store the output value in the known conditions and use that value during measurements to offset against the measured value. Alternately during calibration the heating elements on the first and/or membrane maybe biased slightly differently until the output is zero. The required bias value to get zero output in the calibration condition may then be stored, and the same bias used on the first and/or second membrane during measurement.

The temperature sensing elements may be located in a same layer of the dielectric region as the heating element and the temperature sensing elements may laterally surround the heating element.

Alternatively, the temperature sensing elements may be located below or above the heating element. The temperature sensing elements may be located directly above or below the heating element, so that the temperature sensing elements are not laterally spaced from the heating element.

Having the temperature sensing elements below or above the heating element has the advantage that the temperature of the temperature sensing elements is substantially the same of that of the heater. This increases the differential signal between the temperature sensing elements of the first and second membrane in the presences of target fluid, therefore improving sensitivity of the sensor. If the temperature sensing elements are laterally spaced from the heating element then it is preferred that they be as close together as possible to improve sensitivity.

As described above, in another embodiment of the invention one of the resistive temperature sensing elements in each of the dielectric membranes also acts as the heating element. In this case electronic switches can be used to temporarily disconnect the heating elements from the applied bias and be used to measure the bridge output. The measurement time in this case should be much shorter than the thermal time constant of the membrane, so the turn off time doesn't affect the temperature of the membrane. The advantage of this embodiment is simplicity and reduced number of additional elements on the membrane. The larger the number of elements on the dielectric membrane, the higher the probability of impaired reliability or malfunction of the sensor. The reduced number of elements can also result in reduced power consumption.

In another embodiment of the invention both of the temperature sensing elements in each of the dielectric membranes also act as heating elements. In this case, the temperature sensing elements are part of a wheatstone bridge, and the bias applied to the wheatstone bridge also heats up the membranes. The circuitry in this embodiment can be much simpler than the previous embodiments.

The heating element in all the example embodiments may be a resistive heating element, made of a CMOS compatible material such as aluminium, tungsten, copper, titanium, polysilicon or single crystal silicon. It can also be made from other materials such as platinum or gold, or other semiconductor materials such as Silicon Carbide, Gallium Nitride, Aluminium Gallium Nitride or Gallium Arsenide. Alternately the heating element could be a diode or a transistor.

The temperature sensing elements in example embodiments are resistive temperature sensing elements and may comprise a resistor made of metal (Tungsten, Al, Copper, Platinum, Gold, Titanium) or semiconductor material (Silicon, Polysilicon, Silicon Carbide, Gallium Nitride, Aluminium Gallium Nitride, or Gallium Arsenide or a two dimensional electron gas). The temperature sensing elements should preferably be identical in size, shape and resistance. Or they can be different within the first membrane, but be identical to the corresponding temperature sensing elements within the second membrane. In such a configuration it is easy to get a zero differential signal in the case that the target gas is not present. Alternately they maybe of different size, shape and/or resistance. But in this case the differential signals may not be zero when the target gas is not present, and either there is always an offset in the signal, or calibration maybe required.

For increased sensitivity and stability, such resistive temperature detectors may have a high, reproducible and stable TCR (Temperature Coefficient of Resistance). Secondly, it is preferable that such resistive temperature detectors are linear in temperature (i.e. their resistance varies linearly with the temperature).

However in other embodiments, the temperature sensing elements may not be resistive but can be diodes, or transistors. One type of temperature sensing element may be used or a combination of different types of sensing elements may be used. For example both the membrane may have one resistive temperature sensor each, and one diode temperature sensor each. When used as a combination such as this, the positions on the output circuit (such as a wheatstone bridge) can also be different depending on the types of temperature sensors used so as to achieve the maximum sensitivity. In such a combination, one of the temperature sensors can also be a thermopile.

In case of diodes or transistors, the bridge circuit would comprise diodes or transistors instead of resistors. Resistors can be simpler to fabricate, while diodes & transistors can have the advantage of better process tolerances as compared to resistors.

The fluid sensor may comprise a semiconductor substrate made of a semiconductor material such as silicon, silicon carbide or Gallium Nitride, and comprising an etched portion. The fluid sensor may also comprise a dielectric region comprising of oxides and/or nitrides such as silicon dioxide and silicon nitride, where the portion of the dielectric region adjacent to the etched portion is referred to as a dielectric membrane. The dielectric membrane may have embedded structures made of semiconductor material or metal structures.

The semiconductor substrate may be any semiconductor such as silicon, silicon on insulator (SOI), Silicon Carbide, Gallium Nitride or Diamond. In particular, the use of silicon is advantageous, as it guarantees sensor manufacturability in high volume, low cost and high reproducibility. The use of a silicon substrate could also enable on-chip circuitry for sensor performance enhancement and system integration facilitation. Such on-chip circuitry could be implemented by using analogue or digital or mixed-signal blocks placed outside the dielectric membrane.

The dielectric membrane or multiple dielectric membranes may be formed by back-etching using Deep Reactive Ion Etching (DRIE) of the substrate, which results in vertical sidewalls and thus enabling a reduction in sensor size and costs. However, the back-etching can also be done by using anisotropic etching such as KOH (Potassium Hydroxide) or TMAH (TetraMethyl Ammonium Hydroxide) which results in sloping sidewalls. The dielectric layers within the membrane which could be formed by oxidation or oxide deposition could be used as an etch stop during the DRIE or wet etching processes. The membrane can also be formed by a front-side etch (using most commonly wet etch techniques) or a combination of a front-side and back-side etch to result in a suspended membrane structure, supported only by two or more beams. The membrane may be circular, rectangular, or rectangular shaped with rounded corners to reduce the stresses in the corners, but other shapes are possible as well.

Preferably, the semiconductor substrate may be silicon and the dielectric membrane may be formed mainly of oxide and nitride materials, or oxinitride (a pre-formed combination of oxide and nitride) and where the heater element may be made of a metal such as tungsten, titanium, copper, aluminium, gold, platinum or a combination of those or a semiconductor such as highly doped n type or p type silicon or polysilicon. The heater may have a shape of a meander, spiral or a hotwire.

The dielectric region may comprise a dielectric layer or a plurality of layers including one dielectric layer. The dielectric region may comprise layers of more than one material, such as silicon dioxide, silicon nitride, or aluminium oxide. The heating element may be fully embedded or partially embedded within the dielectric membrane.

The membrane may also comprise one or more layers of spin on glass, and a passivation layer over the one or more dielectric layers. The employment of materials with low thermal conductivity (e.g. dielectrics) enables a significant reduction in power dissipation as well as an increase in the temperature gradients within the membrane with direct benefits in terms of sensor performance (e.g. sensitivity, frequency response, range, etc.). Temperature sensing elements or heaters made of materials such as monocrystalline or polycrystalline semiconductors or metals could be suspended or embedded in the dielectric membrane.

The dielectric membrane may also have other structures made of metal or other conductive or other materials with higher mechanical strength. These structures can be embedded within the membrane, or may be above or below the membrane, to engineer the thermo-mechanical properties (e.g. stiffness, temperature profile distribution, etc.) of the membrane and/or the fluid dynamic interaction between the fluid and the membrane. More generally, these structures can be also outside the membrane and/or bridging between inside and outside the membrane.

Generally speaking, a dielectric membrane region may be located immediately adjacent or above (or below if a flip-chip technology is used) to the etched portion of the substrate. The dielectric membrane region corresponds to the area of the dielectric region directly above or below the etched cavity portion of the substrate. Each dielectric membrane region may be over a single etched portion of the semiconductor substrate. The membrane maybe a "closed membrane", supported by the substrate along its entire perimeter, or can be a bridge type structure—supported by a number of dielectric beams. The membrane can be any shape—circular, square, rectangle, or square/rectangular with rounded corners.

The fluid sensor may be configured to sense or measure a fluid (this may be a gas but could also be a liquid), and the gas may be made of air and the components of interest could be any of $CO_2$, methane or hydrogen or other gases in dry air or humid air. The component of interest can be any fluid that has a different thermal conductivity than that of air.

The disclosed sensor could be applicable to a variety of gases and liquids, but we make specific reference to Carbon dioxide ($CO_2$), methane and hydrogen as these specific gases have thermal conductivity properties which are significantly different from those of air.

A control and measurement unit/circuitry that drives the heater in constant current, constant voltage or constant power mode may be provided. The driving could be preferably in pulse mode, but continuous mode or AC mode are possible.

The circuitry may be located on a same chip as the fluid sensor. Analogue/digital circuitry may be integrated on-chip. Circuitry may comprise IPTAT, VPTAT, amplifiers, analogue to digital converters, memories, RF communication circuits, timing blocks, filters or any other mean to drive the heating element, read out from the temperature sensing elements or electronically manipulate the sensor signals. For example, it is demonstrated that a heating element driven in constant temperature mode results in enhanced performance and having on-chip means to implement this driving method would result in a significant advancement of the state-of-the-art flow sensors. The driving method known a 3ω may be implemented via on-chip means, or any other driving method, such as constant temperature difference and time of flight, needed to achieve specific performance (e.g. power dissipation, sensitivity, dynamic response, range, fluid property detection, etc.). In absence of on-chip circuitry, this disclosure also covers the off-chip implementation of such circuital blocks when applied to a fluid sensor. Such off-chip implementation may be done in an ASIC or by discrete components, or a mix of the two.

The circuitry may comprise one or more of:
a constant current, constant voltage, constant power or constant resistor drive circuit,
a constant current source,
a Wheatstone bridge,
an amplifier, an Analogue to Digital convertor,
a Digital to Analogue Convertor, or
a microcontroller.

Differential signals can be obtained by using a combination of current sources and differential amplifiers, bridge type circuits or other types of subtraction circuits or instrumentation amplifiers.

The fluid sensor may comprise one recessed region within the first dielectric membrane and/or the second dielectric membrane. The recessed regions could be designed such that there are no recessed regions between the temperature sensing elements and the heating elements within a single membrane. Alternately the recessed regions could be designed such that one of the temperature sensing elements is on one side of the recessed region, and another temperature sensing element and a heating element are on the same membrane is on the opposite side of the recessed region.

The recessed regions or discontinuities in the dielectric membrane provide an interruption (or partial interruption) in the thermal conduction path through the solid of the dielectric membrane. This in turn will mean that the heat path will occur more through the fluid above the recess (via conduction and convention) or through the cavity space formed as a result of the recess (mainly through fluid conduction). In both cases (heat above the cavity space or within the cavity space), the heat dissipation will depend on the thermal conductivity of the fluid. This increases the sensitivity of the differential signal to the thermal conductivity of the fluid as a larger percentage of heat loss will be through the fluid.

The one recessed region may comprise one or more discontinuous regions where the thickness of the dielectric membrane is discontinuous or varies from an average or most common dielectric membrane thickness.

The one recessed region may be located between the heating element and an edge of the dielectric membrane.

An edge of the dielectric membrane may refer to a perimeter edge of the dielectric membrane, in other words, the area where the dielectric membrane meets or joins the semiconductor substrate. The area of the dielectric region above the semiconductor substrate may refer to the area of the dielectric region outside the dielectric membrane.

The recessed regions may be holes (perforations) through the dielectric membrane. This would be advantageous, as the thermal conduction path through the solid of the dielectric membrane will be impeded and this will mean that the thermal conduction will occur through the holes (mainly via conduction) or above the holes (via both conduction and convection), thus facilitating the measurement of the composition of the fluid based on the different thermal conductivity of each of the components of the fluid.

There may be one hole through the membrane to connect the upper side of the membrane to the lower side of the membrane via the fluid to be sensed. The one hole also disrupts the thermal conduction path through the solid dielectric membrane, forcing more heat to dissipate via convection and conduction through the environment. The presence of the one hole also helps to reduce the power consumption of the device (for the same heater temperature), because of the reduction in the heat conduction losses (through the solid membrane). Furthermore, the presence of the one hole allows for a lower thermal mass of the membrane thus reducing the time needed for the heater to heat up and cool down.

The one hole or recessed region may be used to enhance the sensitivity/selectivity to any fluid or component of the fluid (e.g. air with a concentration of $CO_2$) with a thermal conductivity that is different to that of a reference fluid or another component of the fluid (e.g. air).

An arrangement and specific design of different holes and different sensing elements is provided to enhance the sensitivity to any fluid or component of the fluid (e.g. air with a concentration of $CO_2$) with a thermal conductivity that is different to that of a reference fluid or another component of the fluid (e.g. air).

The arrangement of different holes or slots (or recessed regions) may be placed symmetrically around the heating element and the temperature sensing elements.

The at least one recessed region may comprise one or more holes. The holes may refer to apertures, perforations or slots extending through an entire height or depth or thickness of the dielectric membrane. This forms a fluid flow path and provides fluid connection between area above and area below membrane.

The at least one of the one or more holes may comprise an elongate slot extending towards opposite edges of the dielectric membrane. The elongate slot may not extend completely to the edges of the dielectric membrane or completely isolate the dielectric membrane either side of the elongate slot. The elongate slot increases thermal isolation across a width of the dielectric membrane of the device. Optionally the elongate slot may be extending in a same direction as one or more heating elements and/or sensing elements. The elongate slots may be, for example, rectangular, square, or semicircle.

The one or more holes may comprise an array of perforations. The perforations may comprise individual holes significantly smaller than a width of the dielectric membrane of the device. The array of perforations may can extend substantially across a width of the device.

The at least one recessed region may comprise a partial recess within the dielectric membrane. The partial recess or trench may extend from a top surface of the dielectric membrane or may extend from a bottom surface of the dielectric membrane. The partial recess may extend partially through a height or depth or thickness of the dielectric membrane. The at least one perforation may be in the form of a trench formed from the top or the bottom surface but not penetrating the other surface.

The discontinuities may be referred to as a gap in the membrane from the top surface to the bottom surface. Though, not as effective in terms of the thermal performance, a discontinuity could also refer to a trench or partial hole created from either the top or the bottom surface (if an upside-down membrane is used) without penetrating the other surface. The advantage of such partial holes is that they could impact less the mechanical strength of the membrane and in some cases they may be easier to be manufactured. Moreover, such partial holes could be used to hermetically seal the bottom side of the membrane or allow no fluid penetration below the membrane.

The at least one recessed region may have a meander shape. In other words, the discontinuity may have a non-standard shape such as a concertina or corrugated shape formed of a series of regular sinuous curves, bends, or meanders.

The location, shape and size of the recessed regions maybe identical on both the first and second dielectric membranes, or maybe different on the two dielectric membranes.

The heating element may be driven at more than one temperature, to increase the selectivity of the device. Gas thermal conductivity varies with temperature, and this variation is different dependent on the gas. In one drive mode, the heater can be driven at a temperature where the thermal conductivity of air and carbon dioxide are identical, and then used to detect another gas (e.g. hydrogen or methane). In this scenario, there will be no unwanted response from carbon dioxide and thus the selectivity of the device is improved. The heater can also be run at the temperature that provides the optimum sensitivity for the gas that is being measured.

The fluid sensor may comprise an array of multiple pairs of dielectric membranes located over multiple etched portions of the semiconductor substrate, each membrane pair having: at least two temperature sensing elements located within the dielectric membrane; a separate heating element, or one of the temperature sensing elements acting as a heating element. Each membrane pair may have its own output circuitry, or there maybe a single output circuitry multiplexed across each membrane pair, or a combination maybe used. Each membrane pair may be operated at a different temperature. Each membrane pair maybe identical, or maybe different from the other membrane pairs.

The fluid sensor may further comprise a covering located on a surface of the sensor, where the covering may comprise a hole configured to allow fluid travel from an outer surface of the covering to a fluid channel above the first dielectric membrane.

The fluid sensor may further comprise a further temperature sensing element located outside the membrane region. The further temperature sensing element may be thermally isolated from the heating element.

An additional or further temperature sensor may be placed outside the dielectric membrane as a reference temperature sensing element to measure the ambient temperature or the temperature of the fluid, and the signal from the further temperature sensor may be used for temperature compensation for a more accurate calculation of the concentration of one or more specific components of the fluid. While the use of two membranes and a wheatstone bridge helps cancel out many common mode effects such as temperature, changes in ambient temperature can still cause changes in device sensitivity. A separate measurement of ambient temperature thus allows more accurate determination of the fluid composition.

The reference temperature sensing element could be integrated on-chip as an extra resistive temperature detector, a diode or a transistor. An ambient temperature sensor could also be provided as part of the ASIC as a VPTAT or IPTAT sensor based on bandgap reference.

The temperature compensation can be done by using both the temperature reading from the additional temperature sensing element and the differential reading between the temperature sensing elements within the first and second dielectric membranes. This can be implemented by either a formula (within an algorithm) to adjust the final reading, or using a look up table and interpolation to determine the final reading.

The second dielectric membrane can be isolated from the surrounding fluid by encapsulating it with a known fluid. The encapsulation can be done on wafer/chip level, or on a package level. The term package is used herein to refer to an assembly or module comprising the fluid sensor and one or more other components mounted to, on or with the fluid sensor, and/or coupled thereto.

In one example, there maybe a small cap with sidewalls and lid attached above the second dielectric membrane, and also a base below the substrate closing off the second cavity portion of the substrate. In this way the second dielectric membrane is isolated from the environment, and will only be in contact with the fluid that it is encapsulated with. The cap and base could be made of a semiconducting material such as silicon. They can also be made of glass, metal or plastic. The cap could also comprise sidewalls made of silicon and lid made of dielectric materials such as silicon dioxide and silicon nitride.

In another example the encapsulation is done on a package level. In this case, the package comprises a base, and a cap such that the package comprises two regions—one region which is sealed, and one which is exposed to the surrounding fluid. The package cap in the exposed region may have one or more holes in it to allow exposure to the surrounding fluid. There may also be a filter in the holes to protect against dust or moisture. A package wall separates these regions. The sensor is packaged such that part of the semiconductor substrate is in the sealed region, and part of the semiconductor substrate is in the exposed region, and the first dielectric membrane within the exposed region, and the second dielectric membrane within the sealed region.

In another example of encapsulation done on package level, the there are two semiconductor substrates, the first semiconductor substrate having a first etched portion and first dielectric membrane, and a second semiconductor substrate having a second etched portion and the second dielectric membrane. The first semiconductor substrate is in the exposed portion of the package, and the second semiconductor substrate is in the sealed region of the package.

The fluid within the sealed can be air, dry air, synthetic, a vacuum, a partial vacuum, an inert gas such as nitrogen or argon or any other fluid mixture of known quantity.

According to a further aspect of the disclosure, there is provided a sensor assembly comprising the fluid sensor as described above and an application specific integrated circuit (ASIC) coupled to the sensor.

The control circuitry can be located on the same chip as the sensor (monolithically integrated), or can have an application specific integrated circuit (ASIC) coupled to the sensor. The ASIC can be on a separate chip, but within the same package, as a hybrid, co-packaged or using system in package (SIP) solutions. Alternatively, the ASIC could be placed outside the package, on a PCB (Printed Circuit Board) or within the same case/box.

The ASIC may be located underneath the sensor, for example using a die stack technique. Alternatively, the ASIC may be located side by side with the sensor or elsewhere. The ASIC may be connected to the sensor using wire bonding and pads, or using through-silicon-vias (TSV) extending through the semiconductor substrate. Alternatively, the sensor and the ASIC can be located on the surface of a common PCB or embedded in a PCB.

An ASIC may be provided within the same system or the same package or on-chip to provide electronic circuitry to drive, read-out signals and process signals from the sensor. The ASIC may be placed in a stack die configuration under the sensor and the sensor and ASIC are placed within a manifold or an open package, to allow contact to the fluid.

According to a further aspect of the disclosure, there is provided a sensor assembly comprising a sensor housing; and a fluid sensor as described above located within the flow sensor housing.

According to a further aspect of the disclosure, there is provided a sensor assembly comprising the fluid sensor as described above, wherein the fluid sensor may be packaged on a printed circuit board in a flip-chip configuration.

The device may be packaged in a metal TO type package, in a ceramic, metal or plastic SMD (surface mount device) package. The device may also be packaged directly on a PCB, or with a flip-chip method. The device may also be embedded in a substrate, such as a customised version of one of the previously mentioned package, a rigid PCB, a semi-rigid PCB, flexible PCB, or any other substrate, in order to have the device surface flush with the substrate surface. The package can also be a chip or wafer level package, formed for example by wafer-bonding.

In particular, the package maybe designed such that there is a surface very close to the membrane, for example in a flip-chip scenario, such that the surface is less than 50 um from the membrane. This increases the power loss through the fluid and improves the sensitivity of the sensor.

According to a further aspect of the disclosure, there is provided a method of measuring a concentration or composition of a fluid using a fluid sensor as described above, the method comprising: applying an electrical bias to the heating element; and monitoring the electrical bias applied to the heating element and using the value of the electrical bias applied to the heating element and the temperature of the first temperature sensing element or the differential signal to determine the concentration or composition of the fluid based on thermal conductivity of the fluid.

Applying an electrical bias to the heating element may comprise applying an electrical bias such that the differential signal between the temperature sensing elements on the first dielectric membrane, and the temperature sensing elements on the second dielectric membrane may be minimised. Minimised may refer to reducing the differential signal to zero or substantially zero.

The electrical power, current, or voltage applied to the heating element may be adjusted to bring to zero or substantially zero the differential signal between the temperature sensing elements on the first dielectric membrane, and the temperature sensing elements on the second dielectric membrane (by varied the heating element power, current, or voltage could be such that the resistances of the temperature sensing elements or the voltages across the temperature detectors are equal). This may be done during the calibration of the sensor or during the operation of the sensor. This could be set as calibrated point, giving a zero differential signal. Alternatively, this could be set during the operation and the heater power/current/voltage could be measured as an indication of the fluid compositions or the concentration of its components The change in the electrical power, voltage or current through the heater may be monitored to measure one or more concentrations of specific components of the fluid based on their different thermal conductivities.

The measurement of the differential signal (for example, the differential resistance) can be performed in a number of ways. A first way is to connect the temperature sensing elements in two branches and applying a constant current to each branch. In the first branch there is a temperature sensing element from the first membrane connected to ground, and a temperature sensing element from the second membrane connected between the constant current source and the temperature sensing element from the first membrane. The second branch has a temperature sensing element from the second membrane connected to ground, and a temperature sensing element from the first membrane connected to a the constant current source and the temperature sensing element from the second membrane. The voltage difference between the junction of the temperature sensing elements will give a differential signal based on the differences in temperatures of the two membranes and can be measured using a differential amplifier. A further method is to use a Wheatstone bridge or other type of bridges. For both these methods, a calibration can be done initially to set a zero point value. This can either set a differential voltage value when the target fluid (or component of the target fluid) is not present, or modify the current to one of the resistors to ensure the differential voltage is at zero when the target fluid is not present. Alternatively, the calibration can be done initially to set a zero point value of the differential signal when the component of the fluid (e.g. $CO_2$) is known (e.g. 400 ppm of $CO_2$ in air) by using an external precision CO2 device (e.g. NDIR sensor).

The method may comprise driving the heating element in pulse mode or AC mode to modulate the temperature of the heating element to vary the differential signal; and using the differential signal to selectively differentiate between different fluid components and/or determine the concentration of the different components.

The temperature of the heating element may be modulated by varying the current, voltage or power to different levels and/or with different electrical pulses in order to selectively differentiate between different fluid components and/or to provide information regarding the concentration of such components.

The temperature of the heater may be modulated and the output from the read out circuit comprising the temperature sensing elements from the first and second dielectric membranes at different temperatures may be assessed against reference values, and the difference between the two may be indicative of the flow composition.

The heating element temperature may be modulated by applying different power levels to increase sensitivity and selectivity to different fluid components based on their thermal conductivity variation with temperature. For example, the difference between the thermal conductivities of $CO_2$ and the air is higher at room temperature than at high temperatures. The opposite is true for Methane, so the difference between the thermal conductivities of methane and the air is lower at room temperature than at high temperatures. Hydrogen has also a different variation of the thermal conductivity with temperature than that of $CO_2$ or air. By running the heater at different temperature levels (i.e. modulating the temperature of the heater), it is entirely possible to differentiate between the contributions of different concentrations of fluid components in the fluid. In this way, for example, Hydrogen and $CO_2$ contributions can be decoupled and their concentration values can be found.

The heater (also referred to as the heating element) may be operated in a pulse mode (e.g. driven with a square wave, sinusoidal wave, Pulse Width Modulated wave (PWM), Pulse Density Modulation, etc.) or continuous mode. The pulse mode has, among others, the advantage of reduced power consumption, reduced electromigration for enhanced device reliability/lifetime, and improved fluid properties sensing capabilities. Pulses could be used in different polarities to further reduce the impact of electromigration on the heating element.

Different drive modes and measurement modes are possible. For example, the heater can be driven using PWM, and the off time of the PWM can be used to measure heater resistance, and/or differential signal. This measurement can be done in a very short time, faster than the thermal time constant of the membrane to avoid self-heating.

Selectively differentiating between different fluid components and/or determining the concentration of the different components may comprise using a neural network.

An algorithm containing machine learning and artificial intelligence may be implemented. For example, the sensor or a fluid sensing system may further comprise a controller or a processing system comprising a neural network. The neural network may be trained using data from different known gases or mixture of gases at different temperatures. The use of a trained neural network to identify known gases or a mixture of gases can improve accuracy, sensitivity and selectivity of the fluid sensor.

The neural network may be trained to recognise the composition of a gas mixture based on the differential signal between the temperature sensing elements of the first and second dielectric membranes. The neural network could be trained using supervised learning based on a set of data of sensor output values for known gas mixtures at a set of heating element temperatures. The inputs to the neural network could be the sensor output values at a predetermined set of temperatures. The neural network may be configured to process each differential signal from the temperature sensing elements of the first and second dielectric membranes in order to determine the components of the gas mixture and the concentrations of each component in the gas mixture. The outputs from the neural network could be the fraction of each gas in the mixture. Synthetic training data could be generated to enhance the training by providing, for example, many more combinations of gases than would be practically realisable in a real laboratory. A support-vector machine could be trained to discriminate between different gases.

The method may comprise: applying a modulated function to the heating element, the temperature sensing elements of the first and second dielectric membranes; measuring the modulation, the time delay, or the phase shift of the temperature signal from the first temperature sensing element or the differential signal between the temperature sensing elements of the first and second dielectric membranes; and determining a concentration or composition of the fluid using the measured modulation, time delay or phase shift.

A transient, modulated, or pulsed signal may be applied to either the heater element or the temperature sensing elements of the first and second dielectric membranes, and the signals from the first or second temperature detectors will consequently be transient, and their time shape, time delay, or phase shift depends on both the thermal conductivity and the thermal diffusivity of the fluid around the sensor and its concentration of particular fluid components with different thermal conductivities and the thermal diffusivities The heaters or the temperature sensing elements of the first and second dielectric membranes can be biased with a transient signal (e.g. AC, square wave, pulsed, step). Using transient based signals, the thermal diffusivity can be determined using the measured values from the first and second temperature sensing elements. In this way, more information can be extracted from the environment.

In a method of transient fluid sensor drive modes, a step change in input current can be applied to the heater and the time constant for the temperature rise in the heater can be measured. This time constant can give information about the thermal conductivity and diffusivity of the environment. Both can be used to identify gas concentration.

In another method of transient sensor drive modes, a sinusoidal wave can be applied to the heater. The change in amplitude and change in phase shift can provide information on thermal conductivity and thermal diffusivity, thus providing information on the gas concentration.

Any of the resistive temperature detectors may be driven in short pulses of power, voltage or current. The temperature sensing elements (resistive temperature detectors) may be driven in a pulse mode (e.g. driven with a square wave, sinusoidal wave, Pulse Width Modulated wave, Pulse Density Modulation, etc.) or continuous mode. The pulse mode has, among others, the advantage of reduced self-heating of the temperature sensing elements, which minimises the noise and increases the sensitivity or the signal to noise ratio.

Whilst several methods are described, any other method of driving the sensor that can provide information on the environment that is being measured may be used.

According to a further aspect of the present disclosure, there is provided a fluid sensing system comprising a fluid sensor as described above; and a controller configured to perform a method as described above.

The fluid sensing system may include a hardware or software interface wherein an algorithm is implemented to facilitate to selectively differentiate between different fluid components and/or to provide information regarding the concentration of such components.

A software algorithm configured to perform any of the methods as described above could be implemented to differentiate between these components and increase sensitivity related to each of the components of the fluids. The software algorithm could be implemented in a local microprocessor. Calibrated data could be stored in a memory device or integrated circuit. Alternatively, the software could be incorporated within an ASIC and driving of the sensor and processing of the signal could be done within an ASIC.

Processing of the signal could also be done remotely in a sensor hub, or on an external server accessed using the Internet (for example, the cloud).

Sampling and averaging of the data, as well as ways to remove outliers from the data could also be used as part of an algorithm and could be implemented in hardware using different electronic components such as micro-controllers, memories or could be done using an ASIC.

Readings from the sensor may be averaged in several ways, for example using a moving mean average or a moving median average. A moving mean average is useful for removing random noise from the signal. A moving median average is useful for removing outliers.

According to a first aspect of the present disclosure, there is provided a fluid sensor for sensing a concentration or composition of a fluid, the sensor comprising at least one semiconductor substrate comprising a first etched portion and a second etched portion; a dielectric region located on the semiconductor substrate, wherein the dielectric region comprises a first dielectric membrane located over the first etched portion of the semiconductor substrate, and a second dielectric membrane located over the second etched portion of the semiconductor substrate, at least two temperature sensing elements on or within the first dielectric membrane, and at least two temperature sensing elements on or within the second dielectric membrane, where the first dielectric membrane is exposed to the surround fluid while the second dielectric membrane is sealed so as to be isolated from the surrounding fluid; wherein there is an output circuit including the two temperature sensing elements from the first dielectric membrane and two temperature sensing elements from the second dielectric membrane that determines the concentration or composition of the fluid based on a thermal conductivity of the fluid.

According to a further aspect of the present disclosure, there is provided a method of manufacturing a fluid sensor, the method comprising: forming a first dielectric membrane located over a first etched portion of a semiconductor substrate semiconductor substrate comprising a first etched portion; forming a heating element located within the first dielectric membrane; forming a first temperature sensing element spatially separated from the heating element, such that the separation between the heating element and the first temperature sensing element introduces a temperature difference between the heating element and the first temperature sensing element, such that a measured temperature of the first resistive element is indicative of a concentration or composition of the fluid based on a thermal conductivity of the fluid.

BRIEF DESCRIPTION OF THE FIGURES

Some embodiments of the disclosure will now be described by way of example only and with reference to the accompanying drawings, in which.

DETAILED DESCRIPTION OF THE PREFERRED EMBODIMENTS

Some examples of the disclosed device are given in the accompanying figures.

Figure 1:
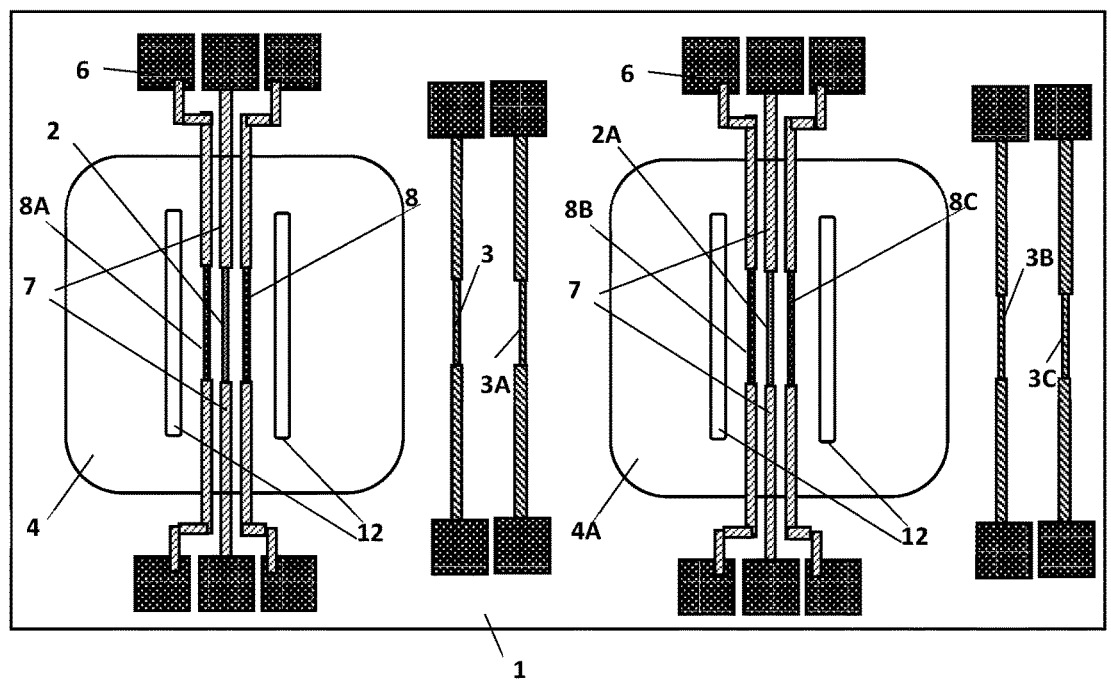
FIG. 1 shows a top view of a thermal conductivity fluid sensor with two membranes, a heating element on each membrane, two temperature sensing elements on each membrane and two temperature sensing elements outside the membrane along side each membrane.
Figure 2:
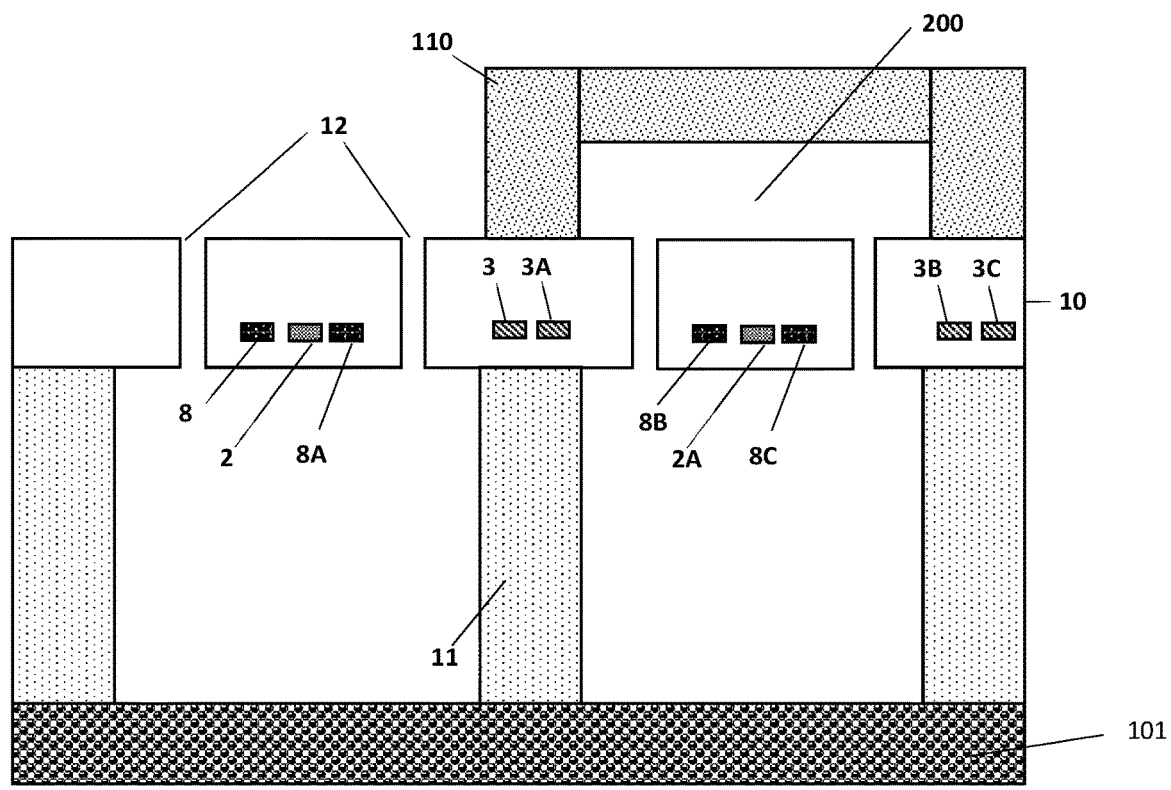
FIG. 2 shows a cross-section of a thermal conductivity fluid sensor with two membranes, where one of the membranes is isolated from the environment.

FIGS. 1 & 2 show the top view and cross-section of a thermal conductivity fluid sensor. It comprises a chip 1 made of a semiconductor substrate 11 and a dielectric layer 10, with a first dielectric membrane 4, and a second dielectric membrane 4A suspended over etched portions of the semiconductor substrate. The first dielectric membrane 4 has a heating element 2 and two resistive temperature sensing elements 8 and 8A. Tracks 7 provide electrical connection from the bond pads to the heating element 2. There are also recessed regions 12 in the shape of slots within the membrane. Similarly the second dielectric membrane 4A has a heating element 2A and two resistive temperature sensing elements 8B and 8C, and recessed regions 12 in the shape of slots. There are a further 4 temperature sensing elements 3, 3A, 3B, 3C on the chip. The chip is attached to a base 101, and a cap 110 is placed over the second dielectric membrane 4A resulting in a sealed region 200, where the fluid (typically but not limited to a gas) is trapped, and the composition of the trapped fluid 200 doesn't change with the change in fluid or environment around the sensor. The first dielectric membrane 4 is exposed to the environment and the thermal behaviour of the membrane changes with change in fluid around the sensor—for example is the fluid composition changes to change the thermal conductivity of the fluid. Hence the power consumption required by the heating element 2 on membrane 4 is affected by change of composition of the surrounding fluid, while the power consumption required by the heating element 2A in membrane 4A does not change.

The membranes 4, 4A are formed by back side etching using DRIE resulting near vertical sidewalls.

For example if the encapsulated fluid 200 is air, and the surrounding fluid is also air, then if the concentration of carbon dioxide in the surround fluid/air increases, the overall thermal conductivity of the surrounding fluid will decrease as the thermal conductivity of carbon dioxide is smaller than air. In that case the heating element 2 on membrane 4 will have slightly lower thermal losses as compared to heating element 2A on membrane 4A. So heating element 2 will require slightly less power to maintain membrane 4 at a target temperature as compared to the power required by heating element 2A to maintain membrane 4A at the same temperature. Alternately if the same bias (current, voltage, power) is applied to both heating elements 2,2A, then membrane 4 will reach a slightly higher temperature than membrane 4A.

Circuitry is used to drive both the membranes to a high temperature. An output circuit uses at least the temperature sensing elements 8,8A,8B,8C to determine the change in fluid composition or the target gas. The circuitry might drive both the heaters 2,2A in a constant bias current, voltage or power. In this case the temperature of membrane 4A will stay the same if there is a change in fluid composition, but the temperature of membrane 4 will change. Using a differential output circuit such as a wheatstone bridge will then give an output based on change in the fluid composition. Using two temperature sensors from each membrane rather than a single temperature sensor from each membrane in the wheatstone bridge means that the sensitivity is doubled as it becomes a half bridge rather than a quarter bridge. Other drive methods can also be used to keep the wheatstone bridge outputting zero volts while adjusting the bias on one of the heating elements 2,2A, and using the bias required to keep the zero output from the wheatstone bridge to determine the fluid composition.

The encapsulated fluid 200 can be air, dry air, synthetic air, an inert gas such as nitrogen or argon. Alternately 200 could be a vacuum or a partial vacuum.

Circuitry to measure the sensor can also comprise two wheatstone bridges, the first wheatstone bridge comprising temperature sensing elements 8,8A,3,3A, and the second wheatstone bridge comprising temperature sensing elements 8B,8C,3B,3C.

In this figure the heating elements are shown as wire heaters, but can be any other shape such as meander, ring, multi ring, circular etc. Similarly the temperature sensing elements can be any shape as well. In this figure the temperature sensing elements and the heating elements are all made from the same material layer and laterally spaced from each other. But they can also be made in different layers, and of different materials, and be either laterally or vertically spaced from each other, and can also be vertically stacked, or a combination. The resistors maybe made of a CMOS metal such as aluminium, tungsten, titanium or copper, or a non-CMOS metal such as gold or platinum, or from polysilicon or single crystal silicon. Similarly the membranes are shown as square with rounded corners, but can be square, rectangle or circular.

Figure 3:
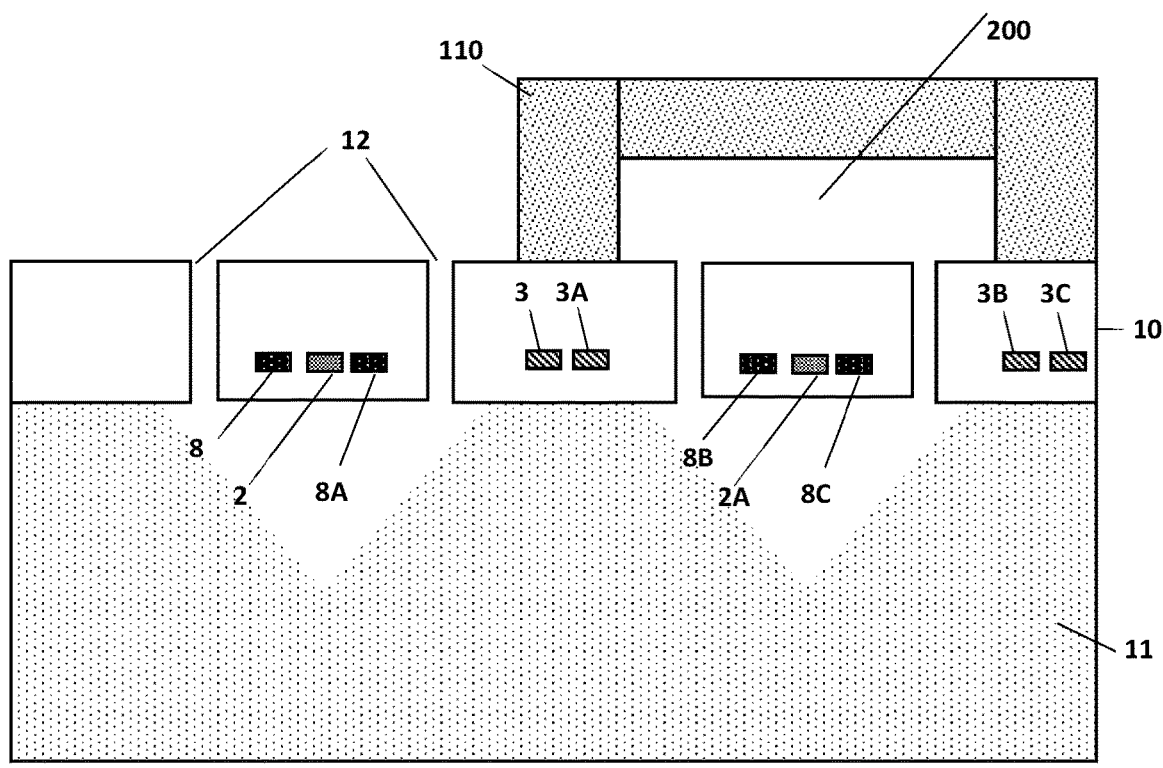
FIG. 3 shows the cross-section of a thermal conductivity fluid sensor with two membranes formed by a front side etch, where one of the membranes is isolated from the environment.

FIG. 3 shows the cross-section of an alternate thermal conductivity fluid sensor where the membranes 4,4A are formed by a front side anisotropic etch such as KOH or TMAH. In this case the etched portions of the substrates do not extend all the way to the bottom of the substrate, rather they stop at the crystal planes of the substrate. Such an etching usually results in a suspended membrane or microbridge, which not supported by the substrate along its entire perimeter, but rather is suspended by one or more beams.

Figure 4:
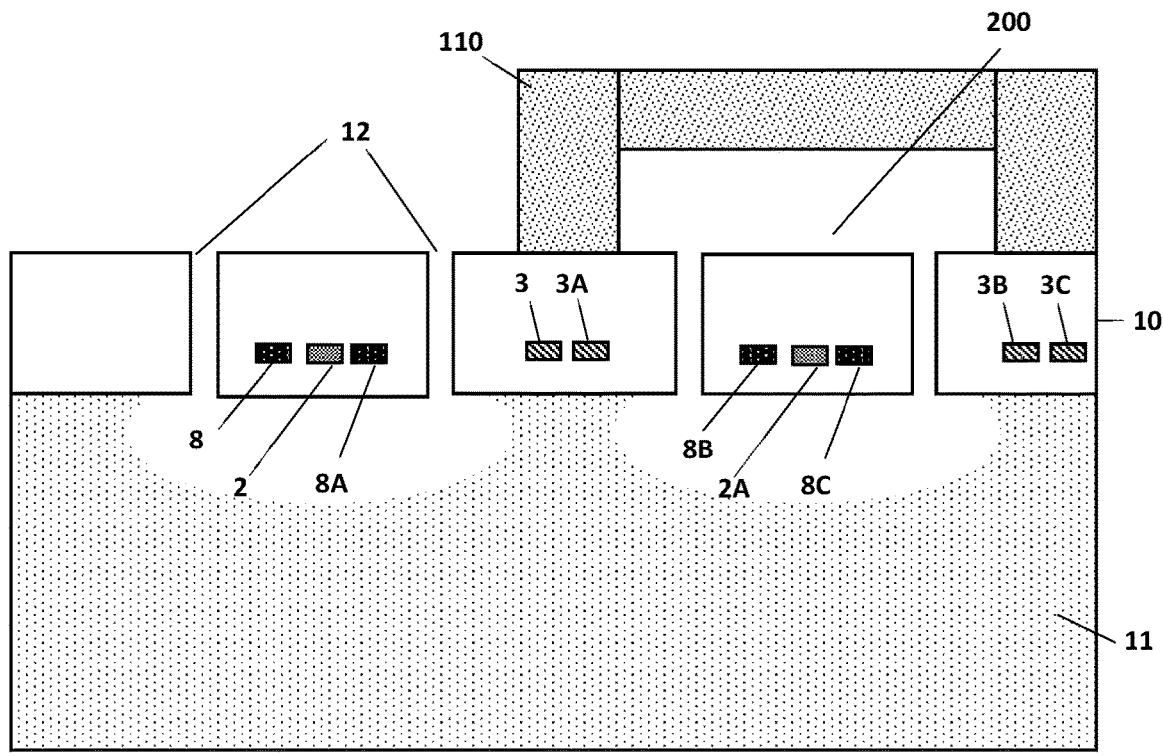
FIG. 4 shows the cross-section of a thermal conductivity fluid sensor with two membranes formed by an isotropic front side etch, where one of the membranes is isolated from the environment.

FIG. 4 shows the cross-section of an alternate thermal conductivity fluid sensor where the membrane 4,4A are formed by a front side isotropic etch which results in curved surface of the substrate etched portion.

Figure 5:
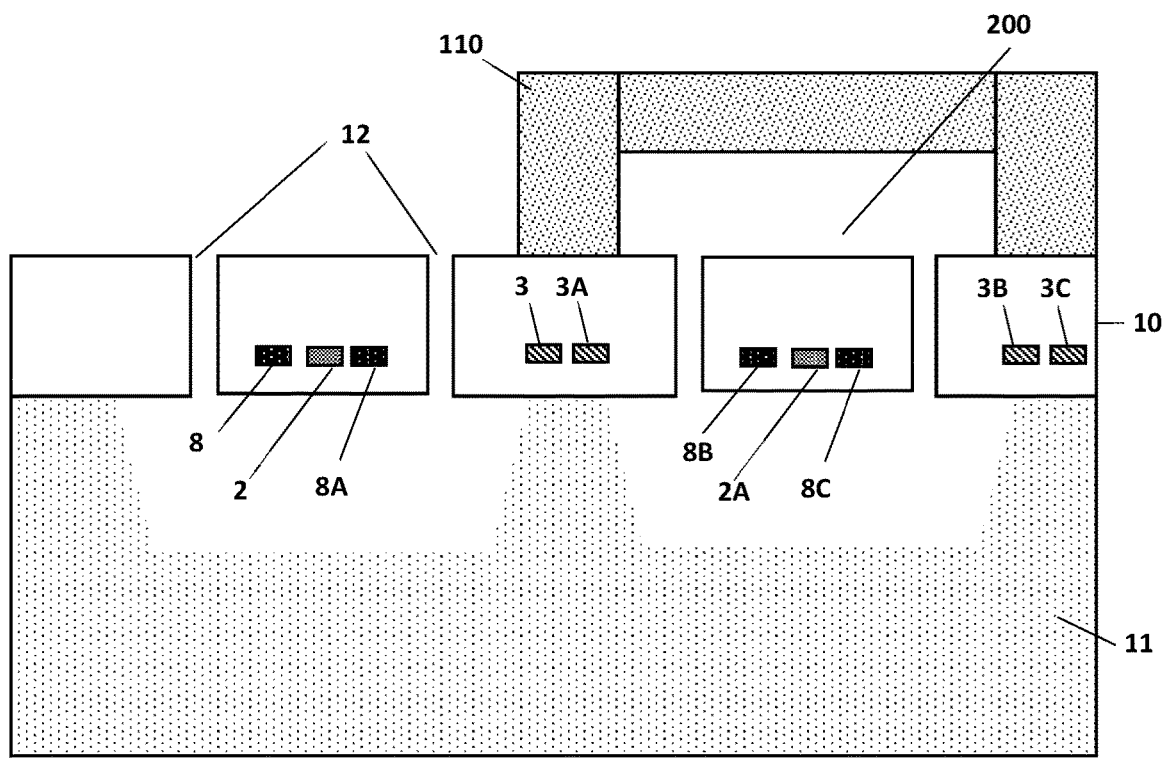
FIG. 5 shows the cross-section of a thermal conductivity fluid sensor with two membranes formed by a timed front side etch, where one of the membranes is isolated from the environment.

FIG. 5 shows the cross-section of a thermal conductivity fluid sensor where the membrane is created by a front side anisotropic etch, but the etch is a timed etch, so as to result in a trapezoid shaped cavity or etched portion within the substrate.

Figure 6:
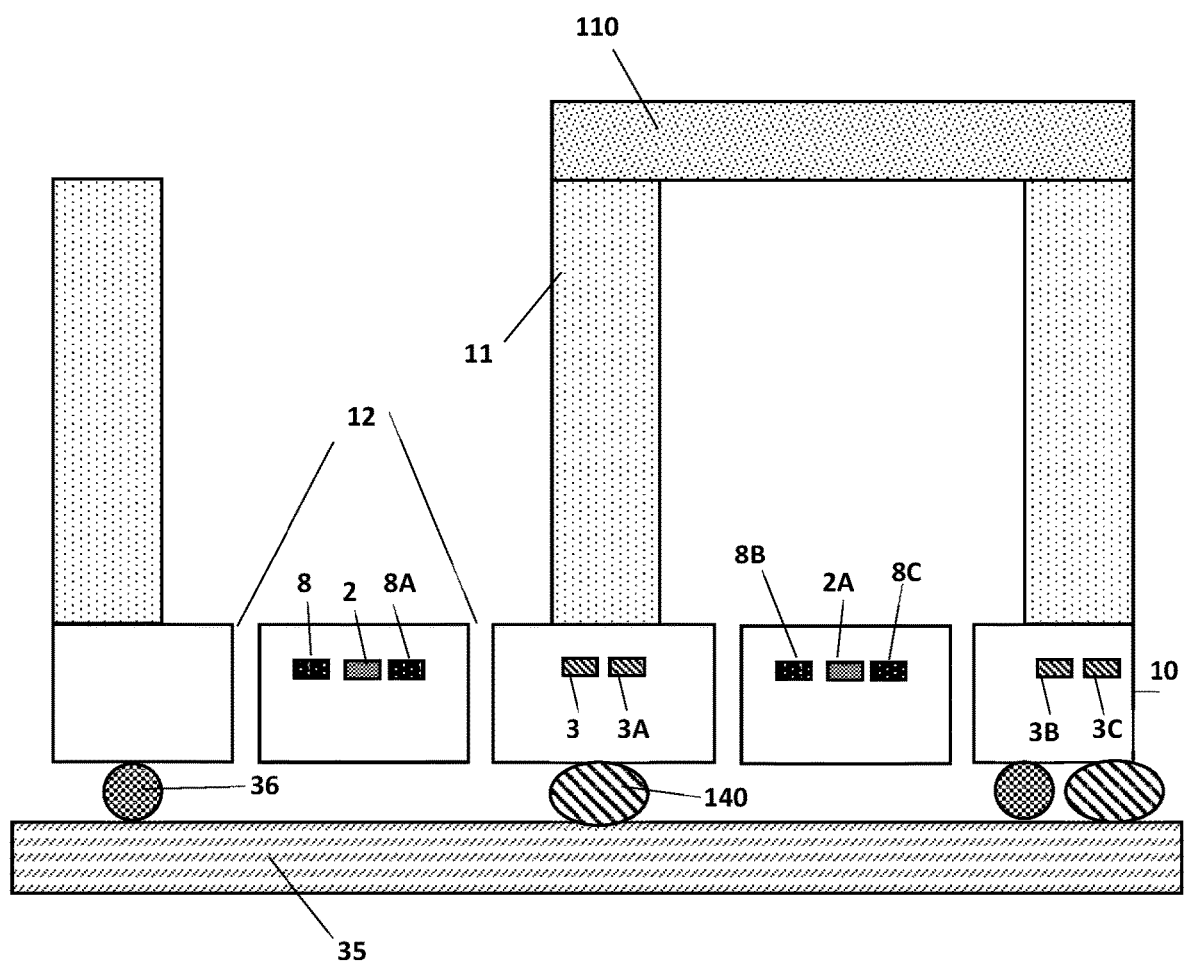
FIG. 6 shows the cross-section of a thermal conductivity fluid sensor with two membranes packaged in a flip chip method.

FIG. 6 shows the cross-section of a thermal conductivity fluid sensor where the chip is packaged in a flip-chip method. In this case the chip is attached to a PCB 35, and electrically connected by the use of solder balls 36. Membrane 4A is sealed by a lid 110 to seal the top, and also a sealant 140 to seal the fluid between the membrane and the PCB. The sealant 140 can be a polymer. It can also be a mixture of components and materials such as a rubber/glass/metal ring coated with a polymer.

Figure 7:
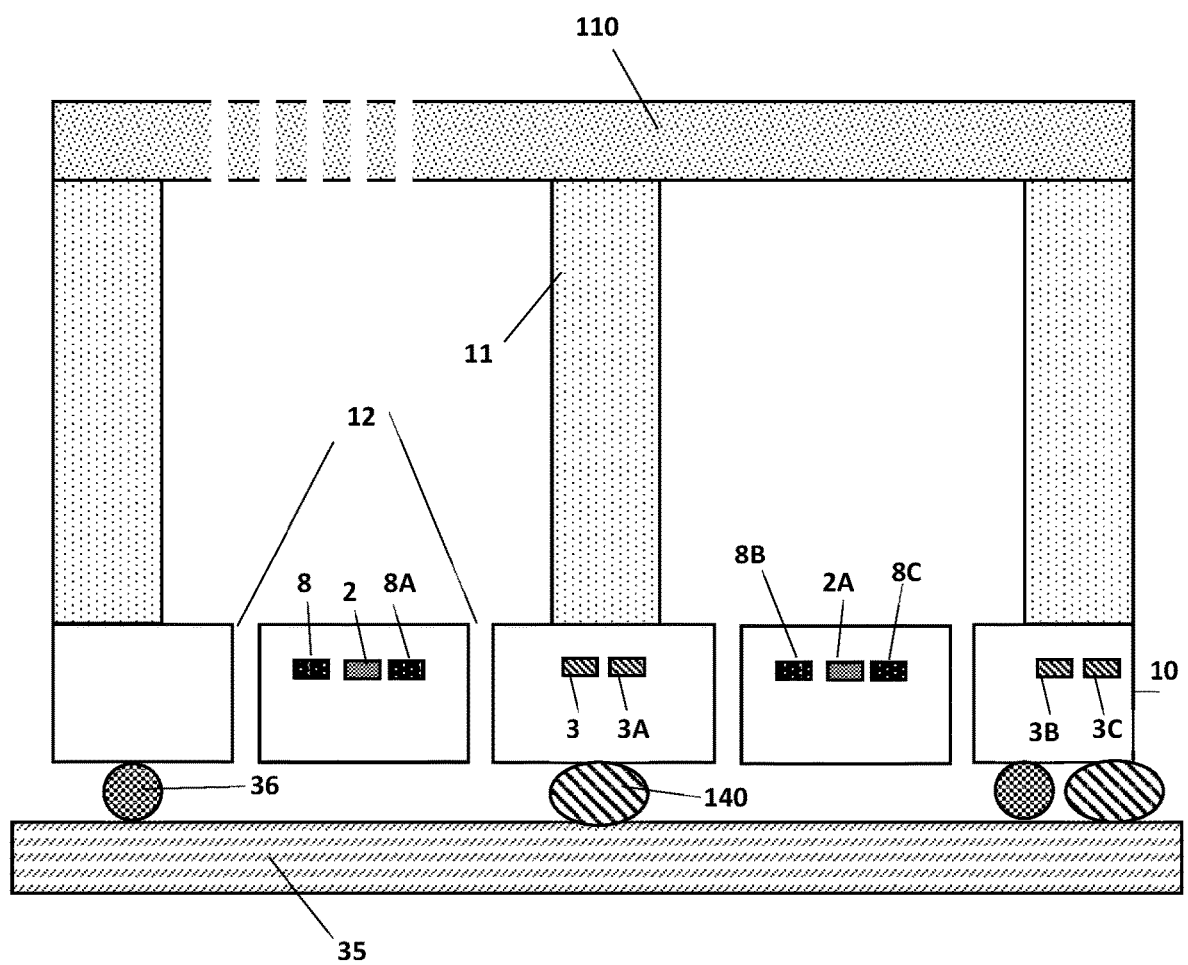
FIG. 7 shows the cross-section of a thermal conductivity fluid sensor with two membranes packaged in a flip chip method where the membrane exposed to the environment has an encapsulation with holes.

FIG. 7 shows the cross-section of another example of a thermal conductivity fluid sensor in a flip-chip package, where the lid 110 extends to the cavity portion of the exposed membrane as well, but there are holes in that portion of the lid to allow exchange with the surrounding fluid. The holes can help protect the membrane during handling, and also dust or moisture. Additional filters may also be added to protect against particles or moisture.

Figure 8:
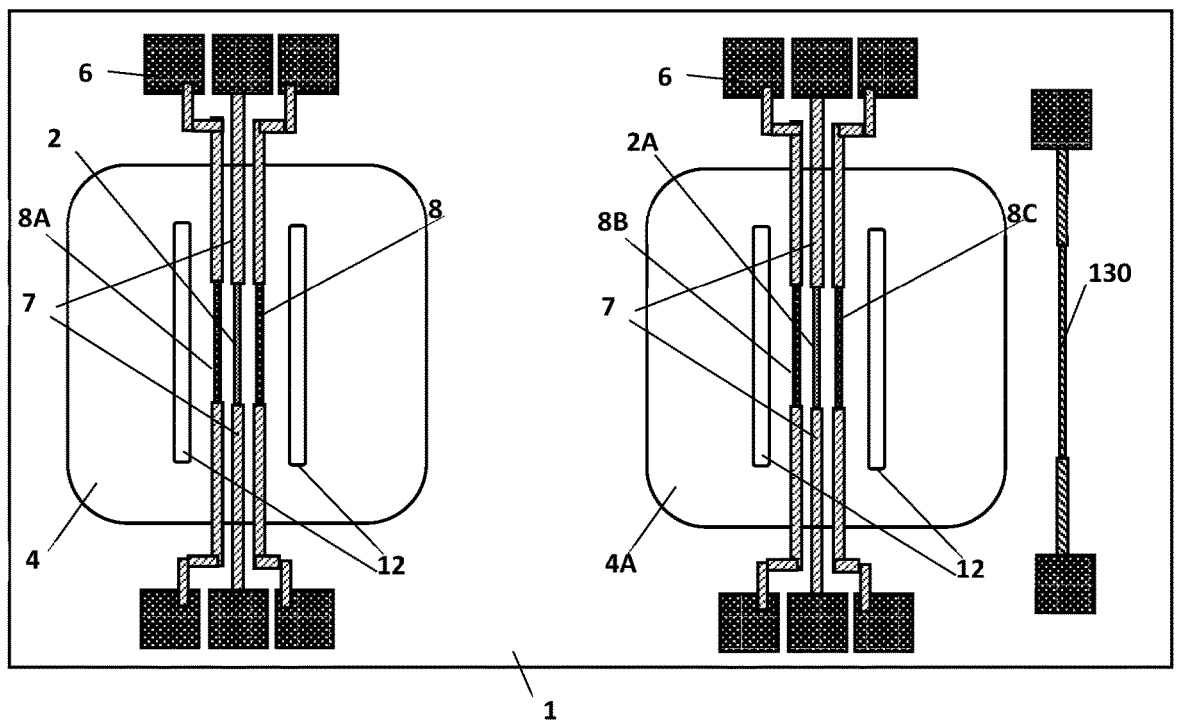
FIG. 8 shows a top view of a thermal conductivity fluid sensor with two membranes, a heating element on each membrane, two temperature sensing elements on each membrane and an ambient temperature sensor outside the membranes.

FIG. 8 shows the top view of another example of a thermal conductivity fluid sensor there is only one temperature sensing element 130 outside the membrane. The temperature sensing element 130 is used to measure the ambient temperature and helps provide a temperature compensation to the measured value of the fluid composition. The temperature sensing element shown in this example is a resistive temperature sensor, but can also be a diode, transistor a VPTAT or IPTAT circuit.

Figure 9:
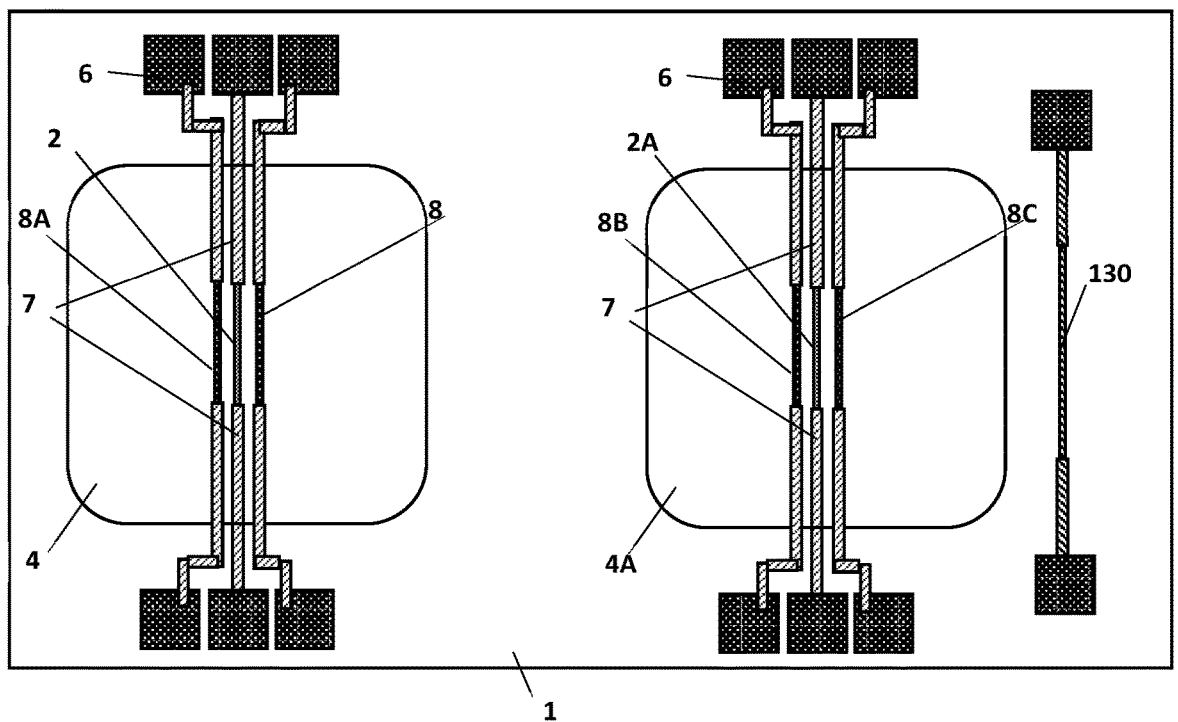
FIG. 9 shows a top view of a thermal conductivity fluid sensor with two membranes, a heating element on each membrane, two temperature sensing elements on each membrane and an ambient temperature sensor outside the membranes with no slots on the membranes.

FIG. 9 shows the top view of another example of a thermal conductivity fluid sensor where there are no recessed regions within the membrane.

Figure 10:
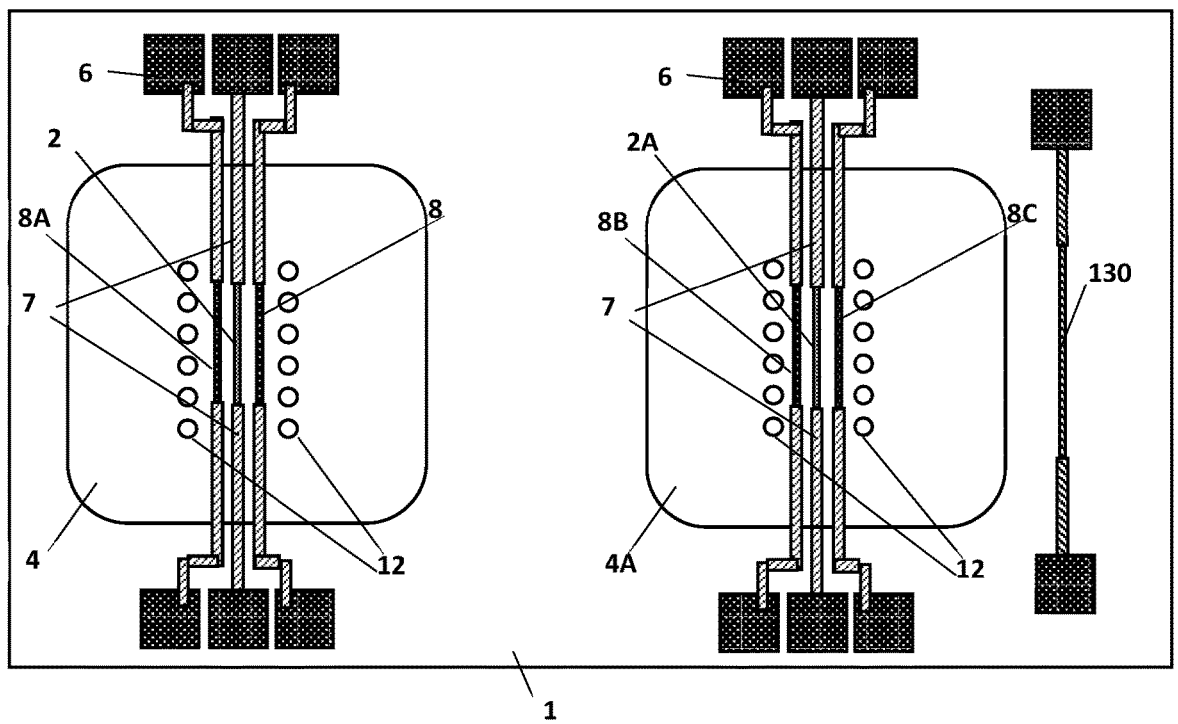
FIG. 10 shows a top view of a thermal conductivity fluid sensor with two membranes, a heating element on each membrane, two temperature sensing elements on each membrane and an ambient temperature sensor outside the membranes with an array of holes on the membranes.

FIG. 10 shows the top view of another example of a thermal conductivity fluid sensor where the recessed regions 12 are an array of holes rather than slots. It should be noted that while FIGS. 8 and 10 show two examples or recessed regions many other shapes and sizes of recessed regions are possible. The recessed regions can also be in different locations on the membrane.

Figure 11:
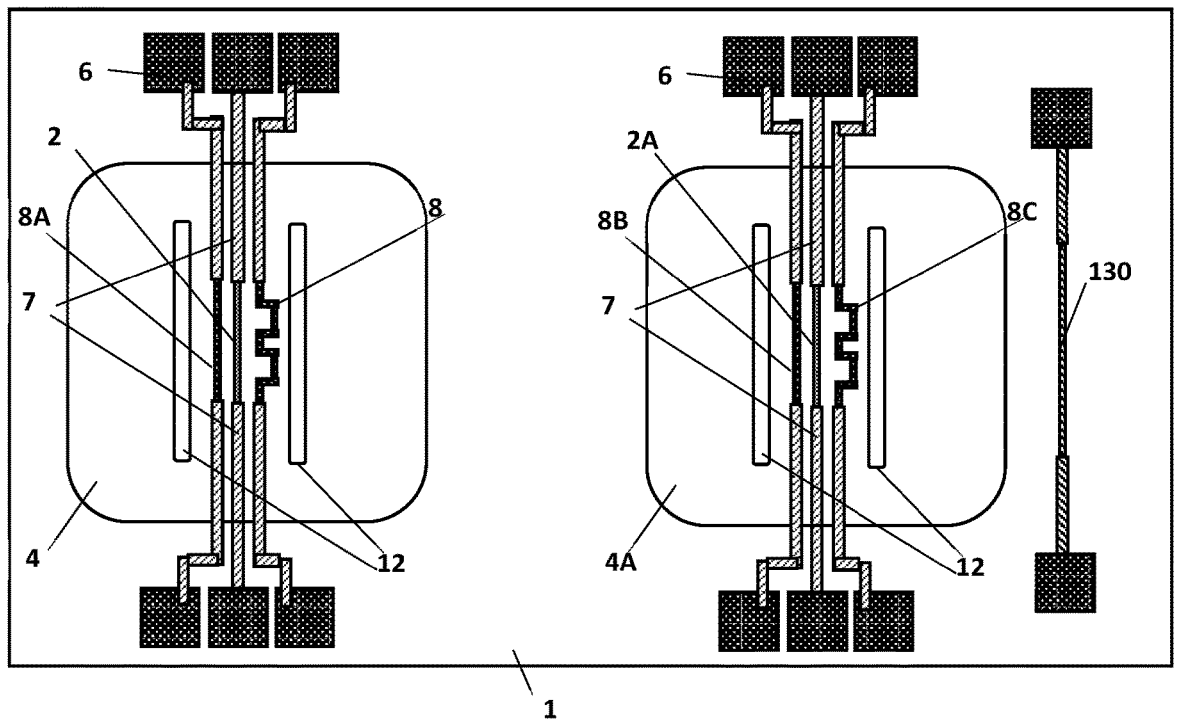
FIG. 11 shows a top view of a thermal conductivity fluid sensor with two membranes, a heating element on each membrane, two temperature sensing elements on each membrane and an ambient temperature sensor outside the membranes, where the temperature sensing elements within each membrane are different.

FIG. 11 shows the top view of another example of a thermal conductivity fluid sensor where the temperature sensing elements 8 and 8A have a different shape and resistance value. Similarly temperature sensing elements 8B and 8C are also different. But element 8 is identical to element 8C and element 8A is identical to element 8B. In this case although the temperature sensing elements within membrane 4 are different, they are identical to the corresponding temperature sensing elements of membrane 4A. The output circuit can still measure the differential signal across these temperature sensing elements as they are identical in the different membranes.

Figure 12:
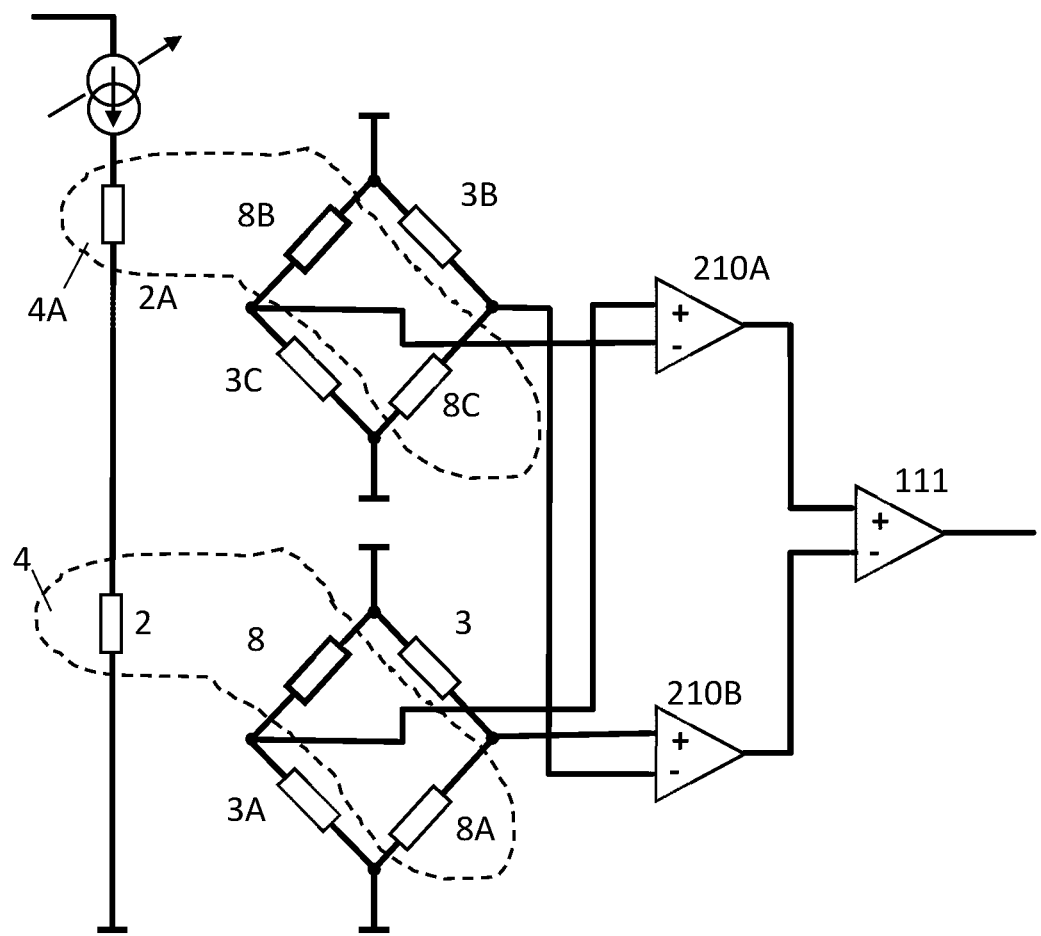
FIG. 12 shows a circuit diagram of a thermal conductivity sensor comprising two wheatstone bridges.

FIG. 12 shows circuitry for driving the thermal conductivity fluid sensor and measuring the output from the thermal conductivity fluid sensor shown in FIG. 1. Heating elements 2, 2A are both driven by a constant current source. The output circuit comprises two wheatstone bridges. One bridge comprises temperature sensing elements 8, 8A from the first membrane, and temperature sensing elements 3,3A. The other bridge comprises temperature sensing elements 8B, 8C from the second membrane. Instrumentation amplifier 210A gets inputs from the left branch of both the wheatstone bridges, while instrumentation amplifier 210B get inputs from the right branches. These then feed into instrumentation amplifier 111.

Figure 13:
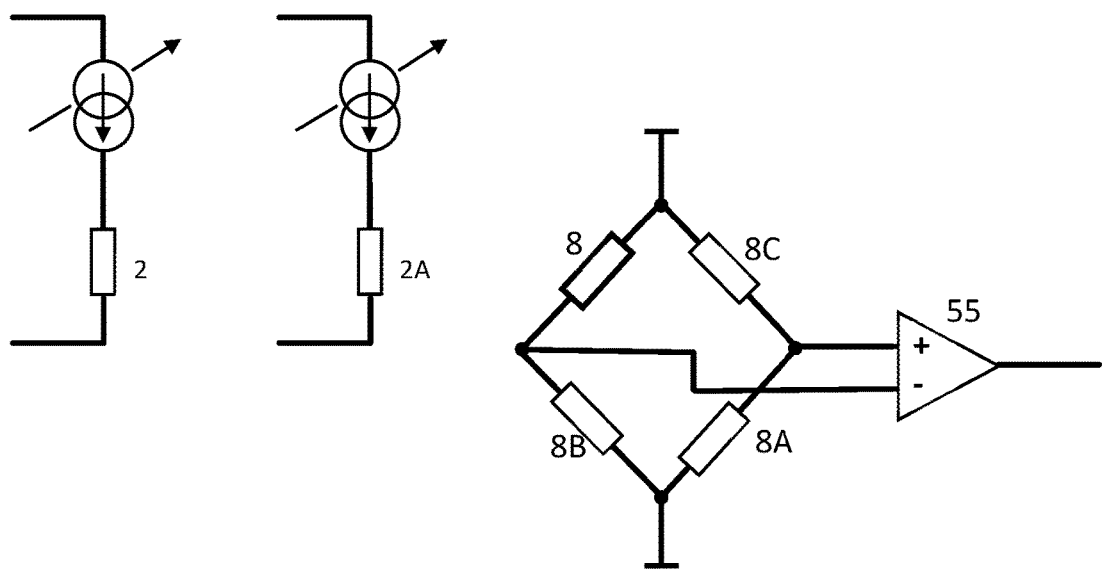
FIG. 13 shows a circuit diagram of a thermal conductivity sensor comprising a single wheatstone bridge.

FIG. 13 shows circuitry for driving the thermal conductivity fluid sensor and measuring the output from the thermal conductivity fluid sensor shown in FIG. 8. Heating elements 2, 2A are driven by constant current sources. The output circuit comprises a wheatstone bridge with temperature sensing elements 8,8A, 8B, 8C, and an instrumentation amplifier 55. If an identical current source is applied to both heating elements 2, 2A, then in normal conditions the temperature of both the membrane 4,4A will be the same, resulting identical resistance of the temperature sensing elements 8,8A, 8B, 8C, giving a zero volt output on the output circuit. However if the surround fluid changes, for example to have a higher concentration of carbon dioxide, then the thermal conductivity of the surround fluid will decrease and power losses from membrane 4 will decrease, resulting in a slightly higher temperature than membrane 4A. In this case the temperature sensing elements 8,8A will have a slightly higher resistance than temperature sensing element 8B,8C, resulting in a misbalance in the wheatstone bridge and the output circuitry will give a non-zero output that can be used to determine the concentration of carbon dioxide present.

Figure 14:
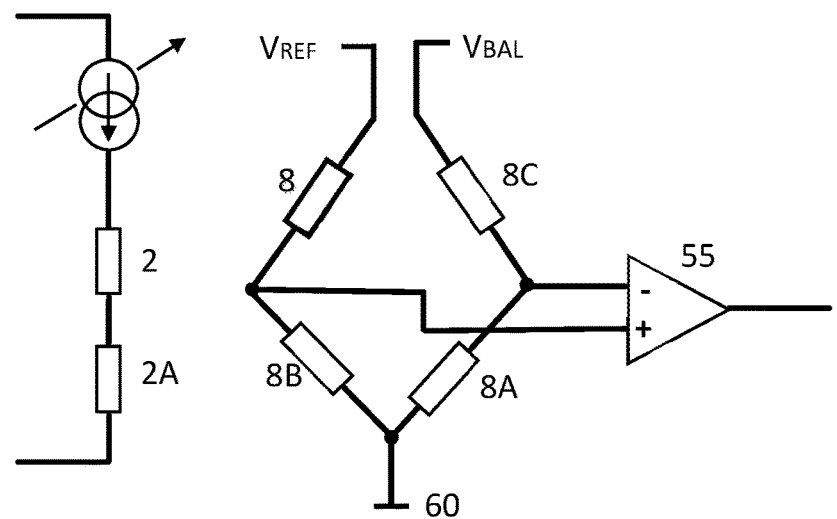
FIG. 14 shows a circuit diagram of a thermal conductivity sensor where a balance voltage can be used to balance the wheatstone bridge.

FIG. 14 shows another example of circuitry to drive and measure the output from the thermal conductivity fluid sensor. Except in this case both arms of the bridge have a different bias voltage. One arm is kept at a constant voltage of Vref, while the voltage to the other arm Vbal can be varied. This can serve many purposes, the main one being in calibration. Due to manufacturing tolerances there maybe some mismatch between the resistive temperature sensors 8, 8A, 8B, 8C and when Vref and Vbal are equal the bridge might still give a non-zero output in normal conditions. So during calibration in a known environment, Vbal is adjusted until the output becomes zero. This value of Vbal is stored, and is also applied when making a measurement.

Figure 15:
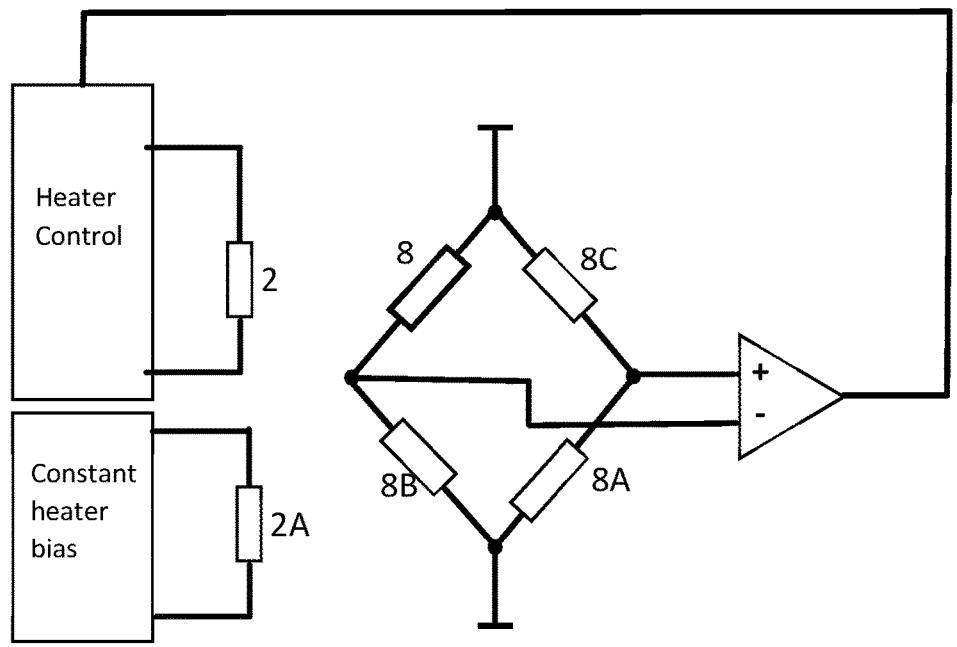
FIG. 15 shows a circuit diagram of a thermal conductivity sensor with a feedback circuit to control the heater.

FIG. 15 show another example of circuitry to drive and measure the output from the thermal conductivity fluid sensor. In this case there is always a constant bias applied to the heating 2A, but the heating element 2 is controlled by a feedback loop from the wheatstone bridge and amplifier circuit. In this case a heater control circuit varies the bias to heating element 2 until the output from the wheatstone bridge and amplifier is zero, and the bias needed to drive the heating element is then used to determine the composition of the surrounding fluid.

Figure 16:
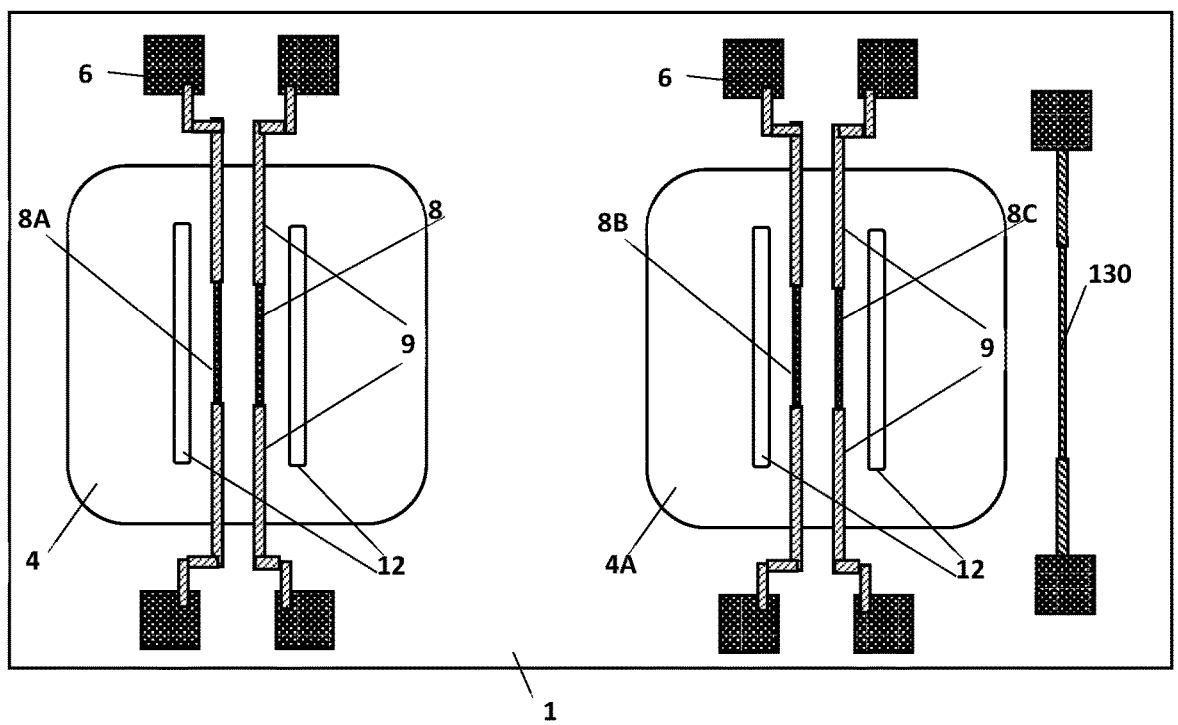
FIG. 16 shows the top view of a thermal conductivity fluid sensor with two membranes and two resistors on each membrane.

FIG. 16 shows the top view of another example of a thermal conductivity fluid sensor comprising two membranes 4, 4A with two temperature sensing elements 8,8A on membrane 4, and two temperature sensing elements 8B,8C on membrane 4A. Unlike FIG. 8, there is no additional heating element on either of the membranes, instead one, or both of the temperature sensing elements can be used as the heating element.

Figure 17:
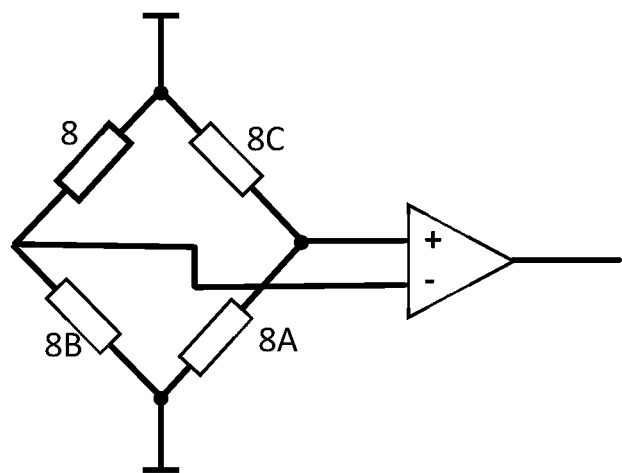
FIG. 17 shows the circuit for a thermal conductivity sensor where there are two resistors on each membrane acting as heating elements and temperature sensing elements.

FIG. 17-20 give some examples of circuits to drive and measure the output from the thermal conductivity fluid sensor. In FIG. 17 both the temperature sensing elements on both the membranes, 8, 8A, 8B, 8C all act as heating elements as well. A bridge circuit incorporates all four elements, and the voltage bias on the wheatstone bridge also provides the bias for heating up the membranes, and also allows a differential measurement between them.

Figure 18:
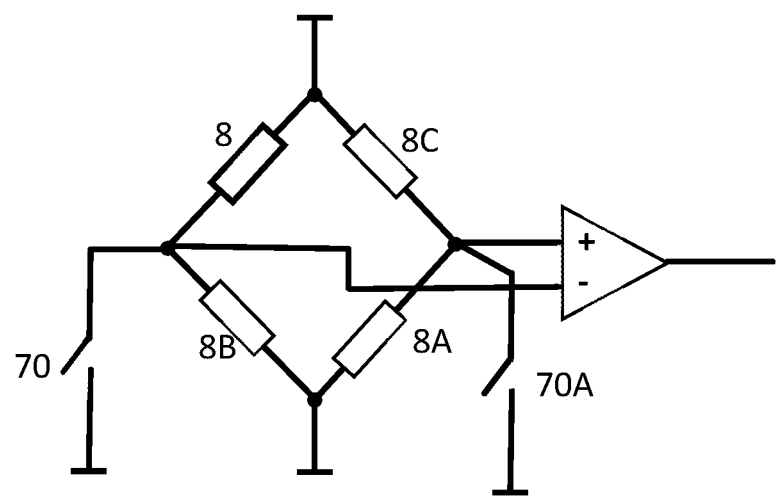
FIG. 18 shows the circuit for a thermal conductivity sensor where there are two temperature sensing elements on each membrane, and one of the temperature sensing elements on each membrane can be switched to also operate as a heating element.

In FIG. 18 the temperature sensing elements 8 and 8C both act as heating elements as well as temperature sensing elements. To operate as heaters switches 70 and 70A are closed, connecting one of the terminal of elements 8, 8C directly to ground. When a measurement is to be made then switches 70, 70A are opened to connect element 8A and 8B as well, completing the bridge. The voltage bias may be lower during the measurement time. The measurement time should be short compared to the thermal time constant of the membranes so that the measurement does not affect the temperature.

Figure 19:
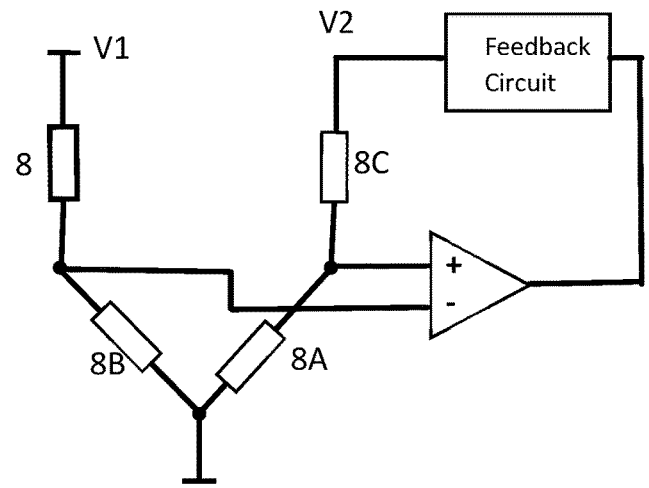
FIG. 19 shows the circuit for a thermal conductivity sensor where the voltage on one of the branches of the wheatstone bridge is controlled by a feedback circuit.

In FIG. 19 all four elements are used as both heaters and temperature sensing elements, but different voltages can be applied to each branch of the wheatstone bridge. Voltage V1 is kept constant while a feedback circuit is used to vary V2. Such a circuit can be used in two ways. In one method the feedback circuit is used in calibration to adjust V2 until the amplifier gives a zero volt output in a known environment, and then the same value of V2 is used always during measurement. In the second method the feedback circuit always varies the value of V2 until the output from the amplifier is zero, and the value of V2 required is used to determine the composition of the fluid.

Figure 20:
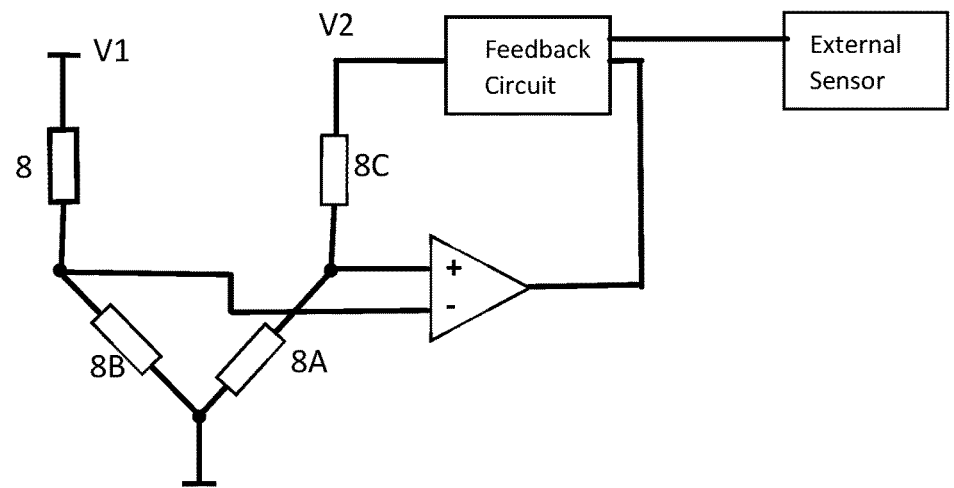
FIG. 20 shows the circuit for a thermal conductivity sensor where the voltage on one of the branches of the wheatstone bridge is controlled by a feedback circuit which also takes input from an external sensor.

FIG. 20 shows another circuit example which is similar to FIG. 19, except the feedback circuit may also use data from one or more external sensors. For example an external measurement of humidity, pressure or temperature can be used to apply an adjustment to the voltage V2 as part of compensating for signal changes due to these factors.

Figure 21:
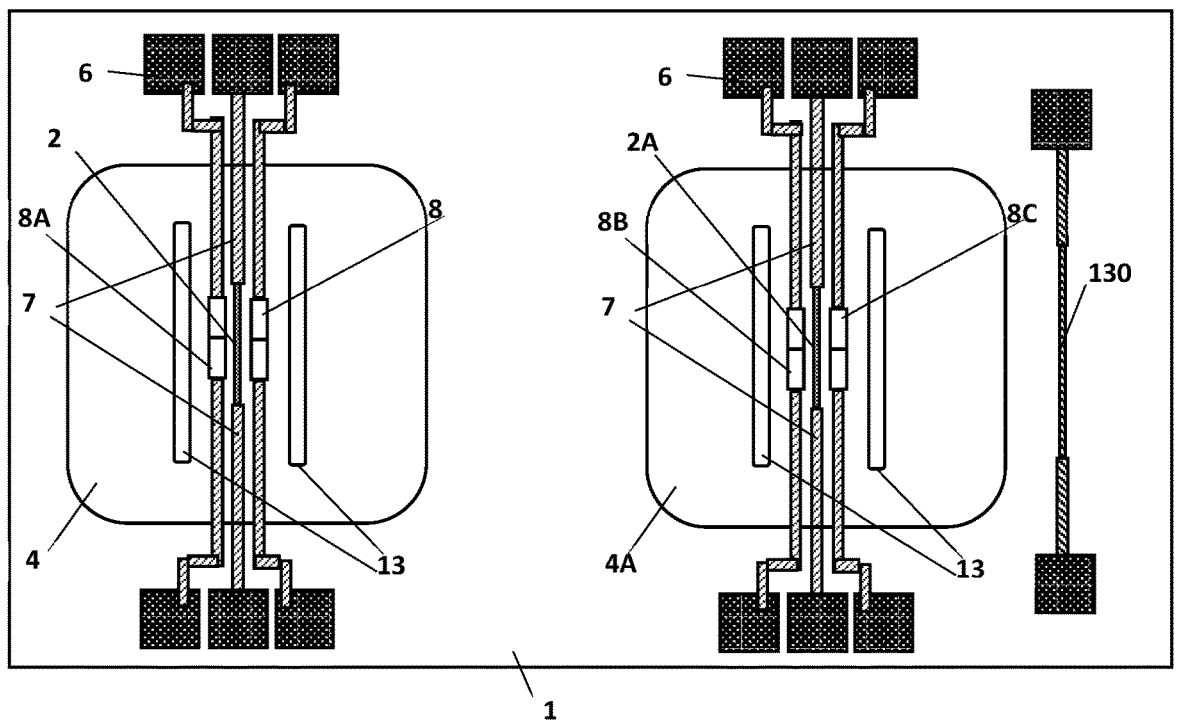
FIG. 21 shows the top view of a thermal conductivity sensor where there are two membranes and each membrane has two diodes that are temperature sensing elements.
Figure 22:
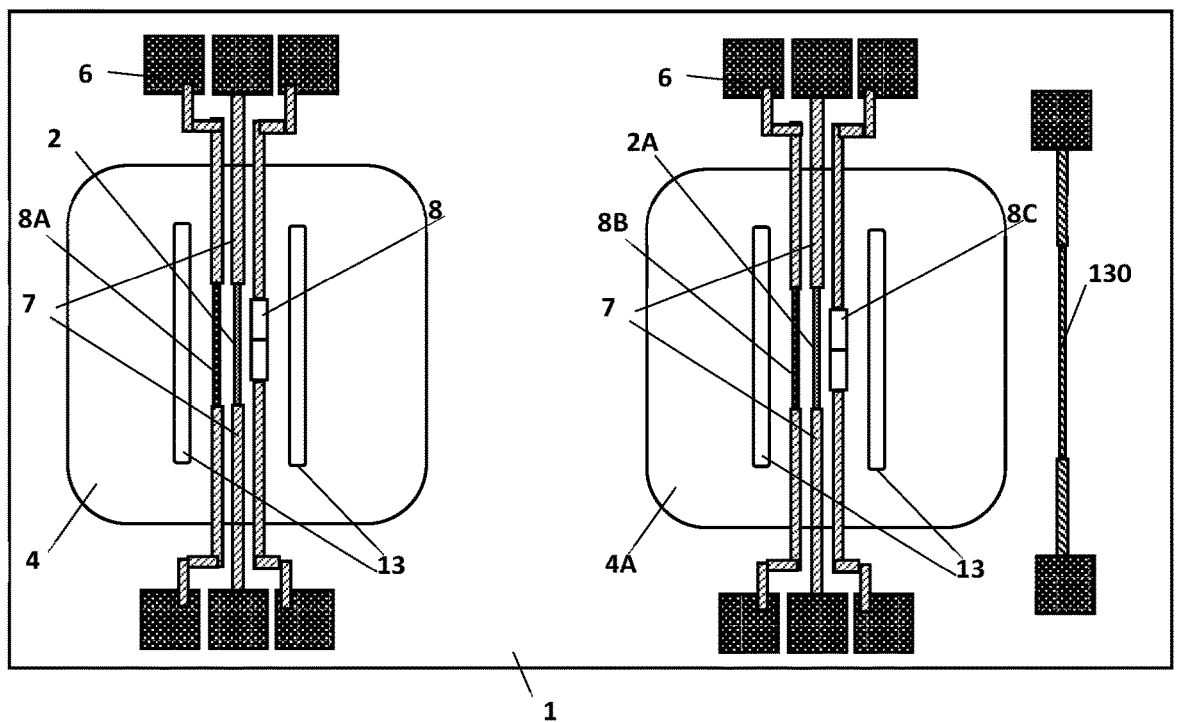
FIG. 22 shows the top view of a thermal conductivity sensor where there are two membranes and each membrane has two temperature sensing elements, one of which is a resistor and one is a diode.

FIG. 21 shows the top view of a thermal conductivity fluid sensor where the temperature sensing elements 8, 8A, 8B, 8C are diodes instead of resistors. FIG. 22 shows an example where one of the temperature sensing element on each membrane is a resistor and one temperature sensing element is a diode.

Figure 23:
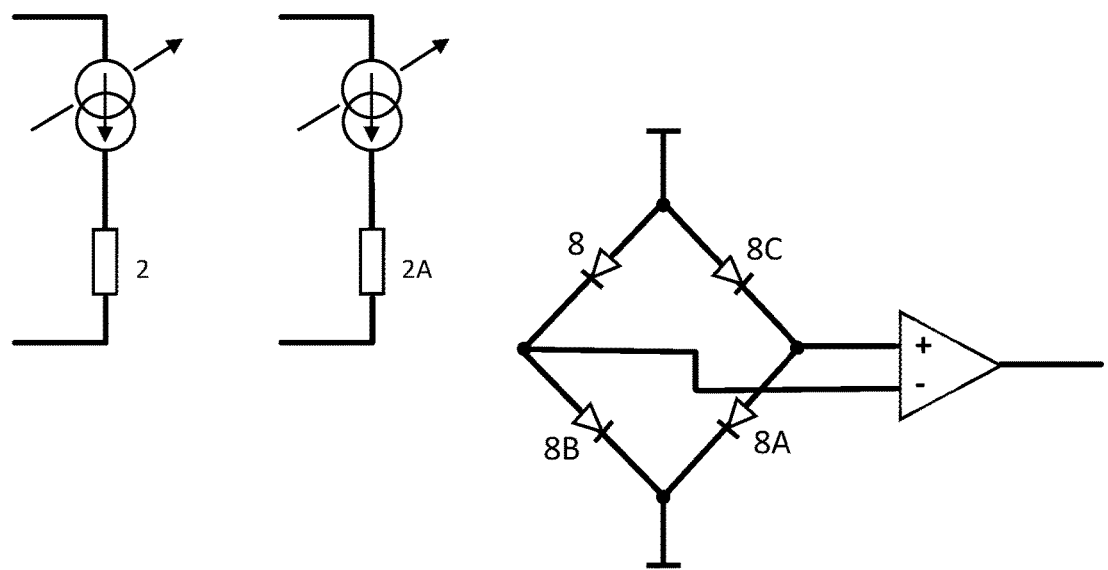
FIG. 23 shows the circuit for a thermal conductivity sensor where the temperature sensing elements are diodes.

FIG. 23 shows an example circuit for the thermal conductivity sensor shown in FIG. 21. This is similar to the circuit with resistors but the resistors are replaced with diodes.

Figure 24:
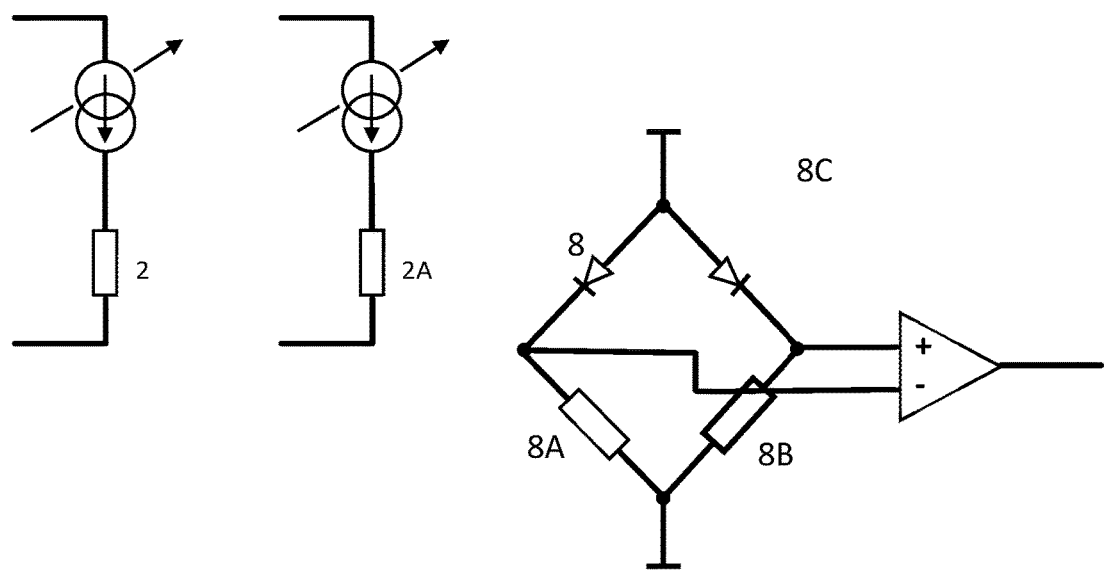
FIG. 24 shows the circuit for a thermal conductivity sensor where the temperature sensing elements are diodes and resistors.

FIG. 24 shows an example circuit for the thermal conductivity sensor shown in FIG. 22. Two of the resistors in the wheatstone bridge are replaced by diodes. However, the connections of the elements is also changed, where elements 8A and 8B are swapped. This is because of the different behaviour of resistors and diodes. During operation if there is more carbon dioxide present, then the temperature of membrane 4 (and hence temperature sensing elements 8, 8A) will decrease. The resistance of temperature sensing element 8A will decrease, while the forward voltage of the diode 8 will increase. In this case its advantageous to have them both in the same branch of the wheatstone bridge as the effect from both will add together.

Figure 25:
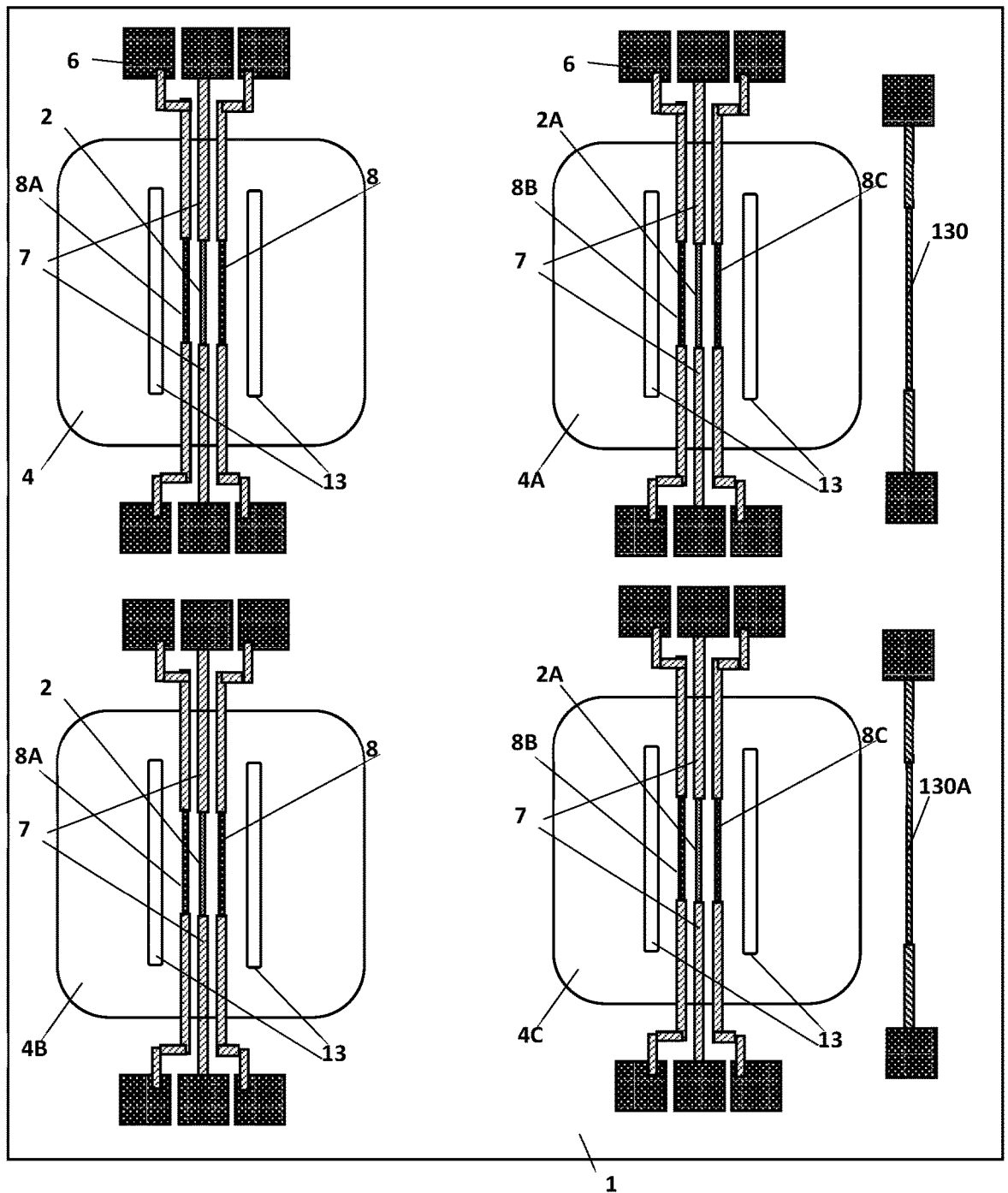
FIG. 25 shows the top view of a thermal conductivity fluid sensor where there are two pairs of membranes.

FIG. 25 shows an example of a thermal conductivity fluid sensor comprising two pairs of membranes (4, 4A) and (4B,4C). In this case each pair can be driven at a different temperature and the data can be analysed to improve the selectivity and accuracy of the sensor.

Figure 26:
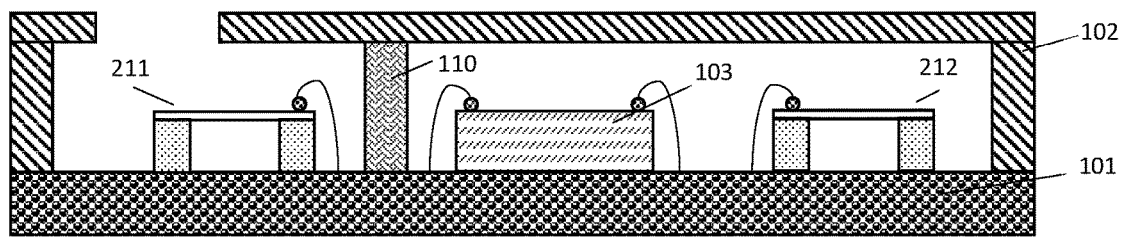
FIG. 26 shows the cross-section of a thermal conductivity fluid sensor package with a sealed region and an exposed region, and two sensor chips and an ASIC chip.

FIG. 26 shows the schematic cross-section of a thermal conductivity sensor package comprising of two sensor chips 111,112 and an ASIC chip 103. The package comprises a base 101, and a lid 102, where the lid has one or more holes. There is a package wall 110 designed such that the package consists of two regions. One region is either hermetically, or semi-hermetically sealed from the ambient environment. The second region has one or more holes in the lid making it open to the environment. The ASIC 103 and one of the sensor chips 112 are placed in the sealed region, and one of the sensor chips 111 is placed in the region open to the environment. Preferably the sensor chips 111 and 112 are identical. In this way sensor chip 112 is always exposed to a known environment, while sensor chip 111 is exposed to the ambient environment, and a differential signal between the two can be used to determine the concentration of the target gas in the ambient environments. The environment in the sealed region can be 100% target gas, a known quantity of target gas in air, synthetic air, pure nitrogen, an inert gas or any other gas or mixture of gases.

Figure 27:
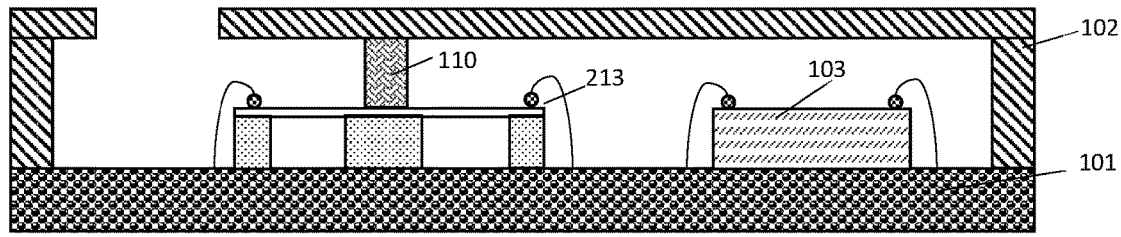
FIG. 27 shows the cross-section of a thermal conductivity fluid sensor package with a sealed region and an exposed region, and one sensor chip and an ASIC chip.
Figure 28:
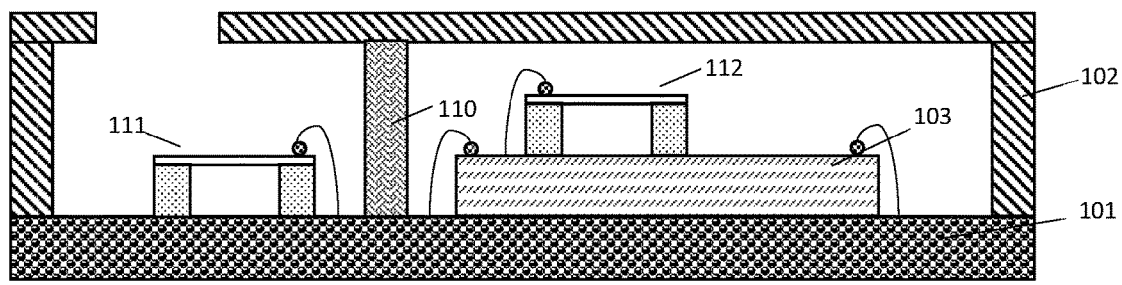
FIG. 28 shows the cross-section of a thermal conductivity fluid sensor package with a sealed region and an exposed region, and two sensor chips and an ASIC chip with one sensor chip stacked on the ASIC chip.
Figure 29:
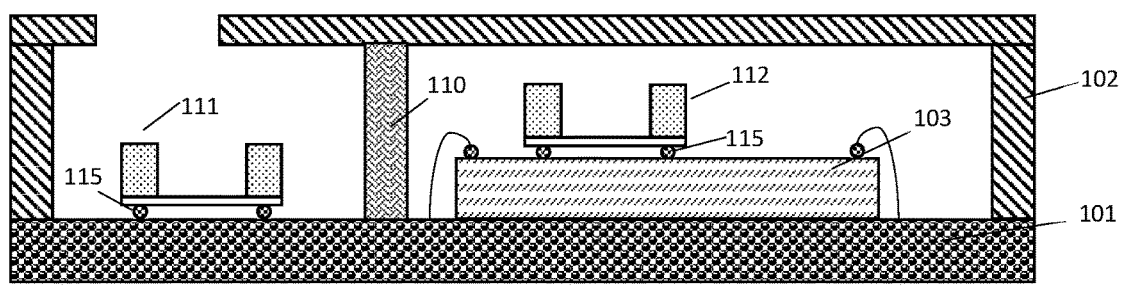
FIG. 29 shows the cross-section of a thermal conductivity fluid sensor package with a sealed region and an exposed region, and two sensor chips and an ASIC chip with one sensor chip stacked on the ASIC chip, and the sensor chips attached in a flip chip method.

FIG. 27 shows the schematic cross-section of a thermal conductivity sensor package comprising a sealed region and an exposed region, but only one sensor chip 113. The wall 110 extend from the lid to the top of chip 113 such that one membrane from chip 113 is in the sealed region, and one membrane is in the exposed region. In this way a single sensor chip can be used while having two regions within the package FIG. 28 shows the schematic cross-section of a thermal conductivity sensor package comprising a sealed region and an exposed region, an ASIC chip 103 and two sensor chips 111, 112 where one of the sensor chips 112 is assembled on top of the ASIC chip 103. In this case the foot print of the package is smaller, while the height can be higher. FIG. 29 show the schematic cross-section of a thermal conductivity sensor package comprising two sensor chips where both the sensor chips 111, 112 are packaged in a flip-chip method. Conductive joints 115 are used to electrically connect the chips to the package or the ASIC. The conductive joints could be solder balls for example. This figure shows the chip 112 above the ASIC, but it could also be side by side with the ASIC and in a flip chip configuration.

Figure 30:
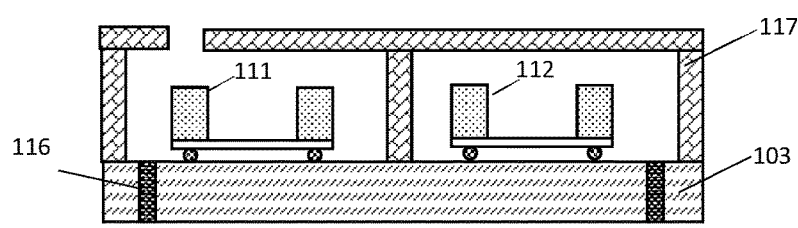
FIG. 30 shows the cross-section of a thermal conductivity fluid sensor package in a chip scale package with the ASIC chip as part of the package.

FIG. 30 shows another schematic cross-section of a thermal conductivity package with the ASIC chip as the package base. In this case a lid 117 is formed on top of the ASIC chip, and designed such that it separates the package in to a sealed region and an exposed region. There is one sensor chip 112 attached to the ASIC chip by flip chip in the sealed region, and one sensor chip 111 attached to the ASIC chip in the exposed region. Through Silicon Vias (TSVs) 116 within the ASIC chip 103 allow electrical connection to the base of the package. Although this figure show the sensor chips connected by flip chip, it is also possible that the sensor chips are right side up and electrically connected to the ASIC by wire bonds.

The skilled person will understand that in the preceding description and appended claims, positional terms such as 'above', 'overlap', 'under', 'lateral', etc. are made with reference to conceptual illustrations of an device, such as those showing standard cross-sectional perspectives and those shown in the appended drawings. These terms are used for ease of reference but are not intended to be of limiting nature. These terms are therefore to be understood as referring to a device when in an orientation as shown in the accompanying drawings.

Although the disclosure has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the disclosure, whether alone or in any appropriate combination with any other feature disclosed or illustrated herein.

REFERENCE NUMERALS

1 Semiconductor chip
2 Heating element
2A Heating element
3 3A, 3B, 3C temperature sensing element outside the membranes
4 Dielectric membrane
4A Additional dielectric membrane
6 Bond pads elements
7 Tracks
8, 8A, 8B, 8C temperature sensing element
10 Dielectric layer
11 Semiconductor substrate
12 Membrane Recess
14 Second dielectric membrane
20 Connecting element
25 Covering layer
26 Fluid channel above membrane
30 Hole through covering layer
35 Printed Circuit Board
36 Solder balls
40, 41 Additional resistor
42, 43 Additional resistor
44 Variable resistor
45, 46, 47 Current source
50 Reference voltage
55 Differential amplifier
60 Ground
65 Field Effect Transistor
70 Switch
75 Ambient temperature sensing element
80 Heater control
100 Pair of temperature sensing elements
101 Package base
102 Package lid
103 ASIC
104, 105 Wire bonds
106 Inlet
107 Outlet
108 Hole through package lid
110 Lid
111 Instrumentation amplifier
115 Solder Balls
116 Through Silicon Vias
117 Lid for a chip scale package
130 Ambient Temperature sensor
140, Sealant for flip chip package
200 Sealed cavity
210A Differential Amplifier
210B Differential Amplifier
211 Sensor die in Exposed Region
212 Sensor die in sealed region
213 Combined sensor chip in package

The invention claimed is:

1. A fluid sensor for sensing a concentration or composition of a fluid, the fluid sensor comprising:
a semiconductor substrate comprising a first etched portion and a second etched portion;
a dielectric region located on the semiconductor substrate, wherein the dielectric region comprises a first dielectric membrane located over the first etched portion of the semiconductor substrate, and a second dielectric membrane located over the second etched portion of the semiconductor substrate;
two temperature sensing elements on or within the first dielectric membrane and two temperature sensing elements on or within the second dielectric membrane; and
an output circuit configured to measure a differential signal between the two temperature sensing elements of the first dielectric membrane and the two temperature sensing elements of the second dielectric membrane;
wherein the first dielectric membrane is exposed to the fluid and the second dielectric membrane is isolated from the fluid; and
wherein one or both of the temperature sensing elements within the first and second dielectric membranes are configured to operate as heating elements.

2. The fluid sensor according to claim 1, wherein the output circuit comprises a wheatstone bridge, wherein the two temperature sensing elements from the first dielectric membrane or from the second dielectric membrane operate as respective first and second legs of the wheatstone bridge.

3. The fluid sensor according claim 2 comprising an ambient temperature sensor on the semiconductor substrate.

4. The fluid sensor according to claim 3, wherein the ambient temperature sensor operates as a respective third or fourth leg of the wheatstone bridge.

5. The fluid sensor according to claim 2, wherein the two temperature sensing elements from the other of the first or second dielectric membrane operate as respective third and fourth legs of the wheatstone bridge.

6. The fluid sensor according to claim 2, wherein the wheatstone bridge is arranged to be balanced by a change of a bias of one or more of a heating element or temperature sensing element operating as a heating element on the first or second dielectric membranes.

7. The fluid sensor according to claim 1, wherein the first and second dielectric membrane comprise a heating element.

8. The fluid sensor according to claim 1, wherein the first and second dielectric membranes have the same size and shape and wherein the temperature sensing elements from the first and second dielectric membranes have the same size and shape.

9. The fluid sensor according to claim 1, wherein the temperature sensing elements comprise one or more of: resistors, diodes, transistors, thermopiles, or a combination thereof.

10. The fluid sensor according to claim 1 wherein the heating elements comprise resistors or transistors.

11. The fluid sensor according to claim 1, wherein the sensor comprises an exposed region exposed to the fluid, and a sealed region sealed and isolated from the fluid.

12. The fluid sensor according to claim 11, wherein the semiconductor substrate comprises separate first and second semiconductor substrate sections, the first semiconductor substrate section comprising the first dielectric membrane on the first etched portion, and the second semiconductor substrate section comprising the second dielectric membrane on the second etched portion, whereby the first semiconductor substrate section is in the exposed region and the second semiconductor substrate section is in the sealed region.

13. The fluid sensor according to claim 11, wherein the semiconductor substrate comprises integral first and second semiconductor substrate sections, the first semiconductor substrate section being in the exposed region and the second semiconductor substrate section being in the sealed region, whereby the first dielectric membrane is in the exposed region and the second dielectric membrane is in the sealed region.

14. The fluid sensor according to claim 11, wherein the sealed region is sealed containing one or more of: air, dry air, synthetic air, an inert gas such as nitrogen or argon, a vacuum, or a partial vacuum.

15. The fluid sensor according to claim 11, comprising an ASIC.

16. The fluid sensor according to claim 15 wherein the ASIC operates as a base of the sensor and comprises one or more through-silicon vias for making electrical connections.

17. The fluid sensor according to claim 1, wherein the sensor is arranged in a flip-chip configuration.

18. The fluid sensor according to claim 1, wherein the output circuit comprises one or more of: a constant current source, a wheatstone bridge, a differential amplifier, an instrumentation amplifier, an analogue to digital convertor and a micro-controller.

19. A fluid sensor assembly comprising:
the fluid sensor of claim 1, and
an ASIC,
wherein the fluid sensor is coupled to the ASIC.

20. A fluid sensor for sensing a concentration or composition of a fluid, the fluid sensor comprising:
a semiconductor substrate comprising separate first and second semiconductor substrate sections, a first etched portion and a second etched portion;
a dielectric region located on the semiconductor substrate, wherein the dielectric region comprises a first dielectric membrane, and a second dielectric membrane;
wherein the first semiconductor substrate section comprises the first etched portion and the first dielectric membrane provided on the first etched portion, and the second semiconductor substrate section comprising the second etched portion and the second dielectric membrane provided on the second etched portion;
two temperature sensing elements on or within the first dielectric membrane and two temperature sensing elements on or within the second dielectric membrane;
an output circuit configured to measure a differential signal between the two temperature sensing elements of the first dielectric membrane and the two temperature sensing elements of the second dielectric membrane; and
wherein the first dielectric membrane is exposed to the fluid and the second dielectric membrane is isolated from the fluid; and
wherein the fluid sensor comprises an exposed region exposed to the fluid, and a sealed region sealed and isolated from the fluid, wherein:
the first dielectric membrane and the first etched portion are in the exposed region; and
the second dielectric membrane and the second etched portion are in the sealed region.

21. A fluid sensor for sensing a concentration or composition of a fluid, the fluid sensor comprising:
a semiconductor substrate comprising integral first and second semiconductor substrate sections, a first etched portion and a second etched portion, wherein the first etched portion and the second etched portion are separated from one another by a portion of the semiconductor substrate;
a dielectric region located on the semiconductor substrate, wherein the dielectric region comprises a first dielectric membrane, and a second dielectric membrane;
wherein the first semiconductor substrate section comprises the first etched portion and the first dielectric membrane provided on the first etched portion, and the second semiconductor substrate section comprising the second etched portion and the second dielectric membrane provided on the second etched portion;
two temperature sensing elements on or within the first dielectric membrane and two temperature sensing elements on or within the second dielectric membrane;
an output circuit configured to measure a differential signal between the two temperature sensing elements of the first dielectric membrane and the two temperature sensing elements of the second dielectric membrane; and
wherein the first dielectric membrane is exposed to the fluid and the second dielectric membrane is isolated from the fluid; and
wherein the fluid sensor comprises an exposed region exposed to the fluid, and a sealed region sealed and isolated from the fluid, wherein:
the first dielectric membrane and the first etched portion are in the exposed region; and
the second dielectric membrane and the second etched portion are in the sealed region.

* * * * *